US011931400B2

(12) United States Patent
Apte et al.

(10) Patent No.: US 11,931,400 B2
(45) Date of Patent: Mar. 19, 2024

(54) THERAPEUTIC AND DIAGNOSTICS COMPOSITIONS TARGETING TOLL-LIKE RECEPTORS AND METHODS THEREOF

(71) Applicant: PSOMAGEN, INC., Rockville, MD (US)

(72) Inventors: Zachary Apte, San Francisco, CA (US); Jessica Richman, San Francisco, CA (US); Daniel Almonacid, San Francisco, CA (US); Melissa Alegria, San Francisco, CA (US); Valeria Marquez, San Francisco, CA (US); Eduardo Morales, San Francisco, CA (US); Rodrigo Ortiz, San Francisco, CA (US); Janet Torres, San Francisco, CA (US); Paulo Covarrubias, San Francisco, CA (US); Javier Gimpel, San Francisco, CA (US); Ingrid Araya, San Francisco, CA (US)

(73) Assignee: PSOMAGEN, INC., Rockville, MD (US)

(*) Notice: Subject to any disclaimer, the term of this patent is extended or adjusted under 35 U.S.C. 154(b) by 140 days.

(21) Appl. No.: 15/914,925

(22) Filed: Mar. 7, 2018

(65) Prior Publication Data

US 2018/0311310 A1  Nov. 1, 2018

Related U.S. Application Data

(60) Provisional application No. 62/536,924, filed on Jul. 25, 2017, provisional application No. 62/468,286, filed on Mar. 7, 2017.

(51) Int. Cl.
| | | |
|---|---|---|
| *C07K 14/00* | (2006.01) | |
| *A61K 38/08* | (2019.01) | |
| *A61K 38/16* | (2006.01) | |
| *G01N 33/68* | (2006.01) | |

(52) U.S. Cl.
CPC ............ *A61K 38/164* (2013.01); *A61K 38/08* (2013.01); *C07K 14/001* (2013.01); *G01N 33/68* (2013.01); *Y02A 50/30* (2018.01)

(58) Field of Classification Search
CPC ..... A61K 38/164; A61K 14/001; A61K 38/08
See application file for complete search history.

(56) References Cited

U.S. PATENT DOCUMENTS

| | | |
|---|---|---|
| 2009/0028889 A1 | 1/2009 | Nakaar et al. |
| 2015/0011532 A1* | 1/2015 | Paidi .................. C07D 413/14 514/210.21 |
| 2015/0213193 A1 | 7/2015 | Apte et al. |
| 2016/0110515 A1 | 4/2016 | Apte et al. |
| 2016/0224748 A1 | 8/2016 | Apte et al. |
| 2016/0232313 A1 | 8/2016 | Apte et al. |

FOREIGN PATENT DOCUMENTS

WO   2016/177797 A1   11/2016

OTHER PUBLICATIONS

EPO, Search Report of 18763116.3 dated Feb. 4, 2022.
Hubert Plovier et al.: "A purified membrane protein from Akkermansia muciniphila or the pasteuyrized bacterium improves metabolism in obese and diabetic mice", Nature Medicine, vol. 23, No. 1, Jan. 1, 2017, pp. 107-113.
Meng Xuan-Yu et al: "Molecular Docking: A powerful Approach for Structure-Based Drug Discovery", Current Computer-Aided Drug Design, , vol. 7, No. 2, Jun. 1, 2011, pp. 146-157.
Liang Shuang et al.: "Mapping of a Microbial Protein Domain Involved in Binding and Activation of the TLR2/TLR1 Heterodimer", The Journal of Immunology, vol. 182, No. 5, Mar. 1, 2009, pp. 2978-2985.
International Application No. PCT/US2018/021404, International Search Report and Written Opinion, dated Aug. 29, 2018, 12 pages.
Koivunen et al., "Identification of Receptor Ligands with Phage Display Peptide Libraries", The Journal of Nuclear Medicine, vol. 40, No. 5, May 1999, pp. 883-888.
Ottman, "Pili-like Proteins of Akkermansia Muciniphila Modulate Host Immune Responses and Gut Barrier Function", PLOS One, vol. 12, No. 3, e0173004, Mar. 1, 2017, pp. 1-18.
"Uncharacterized Protein of Gene Amuc_1100", Uniprot Database Entry B2UR41, Available at: <https://www.uniprot.org/uniprot/B2UR41>, Jul. 1, 2008, 4 pages.

* cited by examiner

*Primary Examiner* — Jeanette M Lieb
(74) *Attorney, Agent, or Firm* — LEX IP MEISTER, PLLC

(57) ABSTRACT

Therapeutic compositions and an associated method for improving a Toll-like receptor (TLR)-related condition, including determining a set of peptide sequences associated with a microorganism-related modulator of a TLR, determining a first set of binding parameters for the set of peptide sequences in relation to the TLR, selecting a target subset of peptide sequences from the set of peptide sequences based on the first set of binding parameters, reengineering the target subset of peptide sequences based on mutating amino acid residues of the target subset of peptide sequences, determining a second set of binding parameters for the reengineered target subset of peptide sequences in relation to the TLR, and identifying a first peptide for use in a therapeutic composition for improving the TLR-related condition, based on the second set of binding parameters for the reengineered target subset of peptide sequences.

12 Claims, 4 Drawing Sheets

Specification includes a Sequence Listing.

one or more instances (e.g., for determining a plurality of components of a therapeutic composition; for refining a therapeutic composition; etc.)

identify modulator S110 modulator (e.g., *Amuc_1100*)

TLR2 determine peptide sequences associated with modulator S120

S130 identify target peptide sequences for reengineering

ADQAPW
PPPIANP
WLGFQVY
FSPPAPI
DFTIFPP
HTPAIFA
AARLTPFSPP
LETAYKPF
AAPAAPAIQQ
HFNQPKAQEP
...

n[X][Z][B]APWn
nPP[X][Z][B][O]Pn
n[X][Z][i][O][B][J][f]n
n[X][J]TAYKP[B]n
n[X]A[J][B]AP[Z][i][O][U]n
nH[X][J]QP[B]AQEPn
n[B]AR[X]TP[Z]SPPn
nF[X]PPAP[J]n
nDFT[X]FPPn
n[X]TPA[J]F[B]n
nXXGFXLKXXn
nXXTPA[ND][NE]XXXn
..

S140 determine binding parameters for reengineered peptide sequences (e.g., apply molecular docking techniques)

extract peptide sequence motifs generate and/or deliver therapeutic composition S150

FIGURE 2

THERAPEUTIC AND DIAGNOSTICS COMPOSITIONS TARGETING TOLL-LIKE RECEPTORS AND METHODS THEREOF

CROSS-REFERENCE TO RELATED APPLICATIONS

This application claims the benefit of U.S. Provisional Application Ser. No. 62/468,286 filed 7 Mar. 2017, and U.S. Provisional Application Ser. No. 62/536,924 filed 25 Jul. 2017, which are each incorporated in its entirety herein by this reference.

INCORPORATION BY REFERENCE OF SEQUENCE LISTING

The Sequence Listing written in file 101215-P30US-0035327_SequenceListing.txt created on Jul. 11, 2018, 9,277,776 bytes, machine format IBM-PC, MS-Windows operating system, in accordance with 37 C.F.R. §§ 1.821- to 1.825, is hereby incorporated by reference in its entirety for all purposes.

TECHNICAL FIELD

This invention relates generally to the field of therapeutics and diagnostics, and more specifically to new and useful therapeutic and diagnostics compositions and associated methods related to detection and/or modulation of toll-like receptors.

BACKGROUND

Toll-like receptors (TLRs) such as TLR2 are integral membrane proteins involved in the functionality of the immune system and/or other physiology. As such, TLRs and their associated mediation of immune responses can have key roles in pathogenesis, the development of, and/or the treatment of TLR-related conditions. For example, TLR2 is involved with hydrocarbon absorption and metabolism (e.g., through regulating expression of Cytochrome P450, family 1, member A1 for detoxifying carcinogenic polycyclic aromatic hydrocarbons, etc.), and has been implicated in immune disorders, metabolic disease, and other TLR-related conditions.

Recognition by the innate immune system is mediated by receptors from different protein families, that is, they are diverse in terms of their sequence and structure. These receptors recognize pathogen-associated molecular patterns (PAMPs). PAMPs are molecular structures present in a large group of microorganisms which have molecular patterns but not a specific structure. That means that these molecular patterns do not display antigenic variability and might be products of microorganism metabolism. On the other hand, the immune system also recognizes damage-associated molecular patterns (DAMPs). DAMPs are endogenous molecules for example, molecules associated to cellular stress or molecules related to tissue damage. In this regard, both PAMPs and DAMPs can be recognized by TLR protein family. In particular, TLR2 recognizes a broad variety of PAMPs and is well-known for forming a dimeric functional structure, as homodimers (e.g., TLR2-TLR2) or even heterodimers with other TLRs (for example, but not limited to: TLR2-TLR6); and thereby increases its range of detection. For example, TLR2 and TLR6 can form heterodimers for detecting bacterial molecules such as peptidoglycan, even when TLR2 can also detect bacterial lipopeptides by itself without TLR6. In another example, TLRs (e.g., TLR2 and TLR4) can regulate an individual's inflammatory response to microbial-related oral conditions including periodontitis, where inflammation of the tissues supporting the teeth can lead to tooth loss. Given the importance of TLRs, modulators of TLRs (e.g., ligands binding to a TLR) or any other molecule potentially able to bind a TLR can help to diagnose and/or treat TLR-related conditions. However, TLRs can be bound by a plethora of different types of ligands. For example, TLR2-binding ligands can include non-acylated peptides and proteins with varied structure and origin. In other examples, TLRs can be bound by ligands derived from a variety of taxonomic groups including archaeal, bacterial, fungal, viral, and/or any other suitable microbiome agent. The number of potential modulators of TLRs can thus be staggering, given that the human microbiome includes up to 10 times more microbial cells than human cells. Further, identification of effective TLR modulators (e.g., modulators derived from microbial products) can be challenging given that the characterization of the human microbiome is still in nascent stages due to limitations in sample processing techniques, genetic analysis techniques, and resources for processing large amounts of data. Nevertheless, TLRs and microbial-related modulators are suspected to play a role in a number of health/disease-related states.

As such, there is a need for therapeutic compositions (and/or processes of identifying such therapeutic compositions) capable of precisely modulating TLRs and/or other suitable receptors in order to improve TLR-related conditions and/or other suitable conditions in patients.

BRIEF DESCRIPTION OF THE FIGURES

FIG. 2 is a schematic representation of variations of embodiments of therapeutic compositions and a method for facilitating diagnosis and/or treatment of a condition (target sequences identified for reengineering=SEQ ID NOS: 198, 693, 35253, 35269, 35271, 35283, 35303, 37718, 35803, and 35839, respectively; extracted peptide sequence motifs=SEQ ID NOS:6-245, SEQ ID NOS:246-693, SEQ ID NOS:694-35253, SEQ ID NOS:35304-35323, SEQ ID NOS:35324-35803, SEQ ID NOS:35804-35839, SEQ ID NOS:35284-35303, SEQ ID NOS:35254-35269, SEQ ID NOS:35270-35271, SEQ ID NOS:35272-35283, SEQ ID NO:1, SEQ ID NOS:2-5, respectively).

DESCRIPTION OF THE EMBODIMENTS

Figure 1:
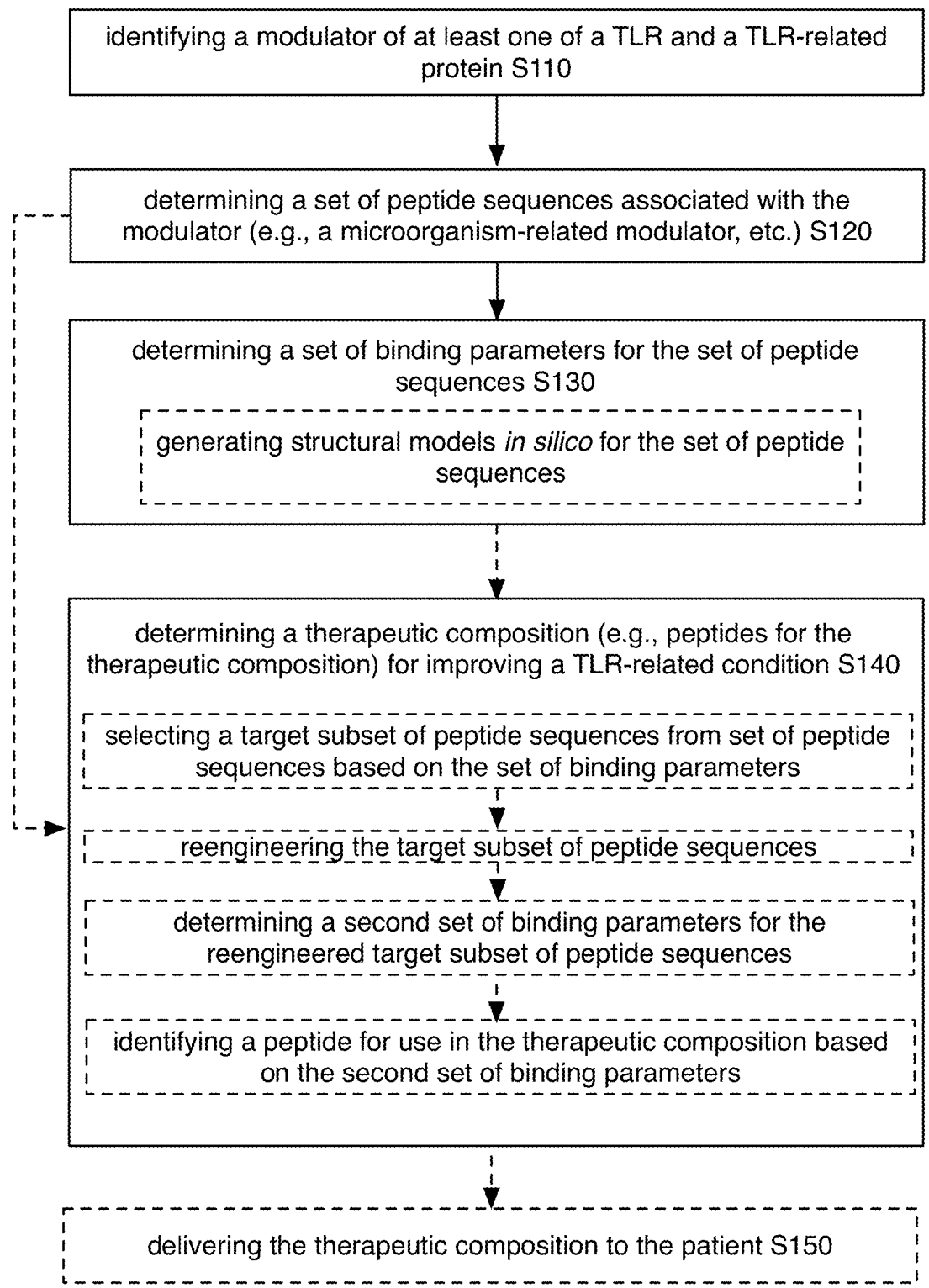
FIG. 1 is a flowchart representation of a variation of an embodiment of a method for determining sequences operable to facilitate diagnosis and/or treatment of a condition.

The following description of the embodiments of the invention is not intended to limit the invention to these embodiments, but rather to enable any person skilled in the art to make and use this invention.

1. Overview

Embodiments of therapeutic compositions for improving a Toll-like receptor (TLR)-related condition can include one or more peptides, such as configured to modulate TLR-related functionality and derived based on reengineering of a target peptide sequence associated with a microorganism-related modulator of a TLR, where the one or more peptides can correspond to peptide sequences derivable from at least one motif of a set of peptide sequence motifs (e.g., where letters in the motifs that are not explicitly defined can correspond to amino acid types defined in Table 12 below and/or can correspond to any one or more of natural amino acids, non-natural amino acids, L-amino acids, D-amino acids, Homo-amino acids, Beta-homo-amino acids, N-methyl amino acids, Alpha-methyl amino acids, unusual amino acids, etc.) including a first motif including XXGFXLKXX (SEQ ID NO:1), where X in the first motif includes any amino acid (e.g., natural amino acids, non-natural amino acids) or no amino acid (e.g., where X is deleted, where one or more mother molecules are inserted, included, and/or otherwise added, etc.); a second motif including XXTPA[Z][B]XXX (SEQ ID NOS:2-5), where X in the second motif includes any amino acid (e.g., natural amino acids, non-natural amino acids) or no amino acid (e.g., where X is deleted, where one or more mother molecules are inserted, included, and/or otherwise added, etc.), where Z in the second motif includes at least one of (N,D), and where B in the second motif includes at least one of (N,E); a third motif including [X][Z][B]APW (SEQ ID NOS:6-245), where X in the third motif includes at least one of (I,F,W,Y,A), where Z in the third motif includes at least one of (D,A,Q,E,G,H,I,L,F,P,T,Y), and where B in the third motif includes at least one of (Q,L,W,Y); a fourth motif including PP[X][Z][B][O]P (SEQ ID NOS:246-693), where X in the fourth motif includes at least one of (Y,P), where Z in the fourth motif includes at least one of (W,Y,F,A,V,C,T,L,S,H,Q,E,G,I), where B in the fourth motif includes at least one of (W,I,F,P,D,G,C,A), and where O in the fourth motif includes at least one of (G,N); a fifth motif including [X][Z][i][O][B][J][f] (SEQ ID NOS:694-35253), where X in the fifth motif includes at least one of (G,Y,W), where Z in the fifth motif includes at least one of (W,V,I,F,R,M,S,L), where i in the fifth motif includes at least one of (I,G), where O in the fifth motif includes at least one of (Y,P,H,L,F), where B in the fifth motif includes at least one of (I,D,Y,F,V,T,G,A,Q), where J in the fifth motif includes at least one of (F,R,C,L,A,Q,D,V), and where f in the fifth motif includes at least one of (F,Y); a sixth motif including F[X]PPAP[J] (SEQ ID NOS:35254-35269), where X in the sixth motif includes at least one of (P,S), and where J in the sixth motif includes at least one of (P,Y,L,A,E,G,V,I); a seventh motif including DFT[X]FPP (SEQ ID NOS:35270-35271), where X in the seventh motif includes at least one of (V,I); an eighth motif including [X]TPA[J]F[B] (SEQ ID NOS: 35272-35283), where X in the eight motif includes at least one of (Y,T,H), where J in the eight motif includes at least one of (H,I), and where B in the eight motif includes at least one of (Y,A); a ninth motif including [B]AR[X]TP[Z]SPP (SEQ ID NOS:35284-35303), where B in the ninth motif includes at least one of (P,A), where X in the ninth motif includes at least one of (A,P,W,N,L), and where Z in the ninth motif includes at least one of (P,F); a tenth motif including [X][J]TAYKP[B] (SEQ ID NOS:35304-35323), where X in the tenth motif includes at least one of (W,L), where J in the tenth motif includes at least one of (A,N,S,W,E), and where B in the tenth motif includes at least one of (S,F); an eleventh motif including [X]A[J][B]AP[Z]I[O][U] (SEQ ID NOS: 35324-35803), where X in the eleventh motif includes at least one of (N,W,A), where J in the eleventh motif includes at least one of (F,N,Y,P), where B in the eleventh motif includes at least one of (P,H,Y,W,A), where Z in the eleventh motif includes at least one of (Y,A), where O in the eleventh motif includes at least one of (W,Q), and where U in the eleventh motif includes at least one of (R,Q); and a twelfth motif including H[X][J]QP[B]AQEP (SEQ ID NOS: 35804-35839), where X in the twelfth motif includes at least one of (E,G,W,F), where J in the twelfth motif includes at least one of (G,A,N), and where B in the twelfth motif includes at least one of (H,W,K).

In examples, therapeutic compositions can include one or more peptides including at least contiguous amino acids derived from at least one of a set of peptide sequence motifs including: XXGFXLKXX (SEQ ID NO:1), and XXTPA[ND][NE]XXX (SEQ ID NOS:2-5), where the notation "X" can indicate any amino acid, a defined set of amino acids, or no amino acid; the non-X letters indicate at least amino acid types described in Table 12 below; the bolded letters can indicate amino acids conserved between the peptide sequence motif and the peptide sequence upon which the peptide sequence motif is based (e.g., peptide sequence of a peptide of microbial-origin) and the notation "[ ]" can indicate additional or alternative amino acids that can be used. In examples, the therapeutic composition can include peptides derived from a peptide sequence motif of xGFXLK (SEQ ID NO:1), where the notation "x" corresponds to any amino acid, but preferably hydrophobic residues (e.g., F, Y, W), and the notation "X" can indicate any amino acid (e.g., natural amino acids, non-natural amino acids) or no amino acid (e.g., where X is deleted, where one or more mother molecules are inserted, included, and/or otherwise added, etc.). In specific examples, the therapeutic composition can include one or more peptides with sequences of any one or more of sequences described in Table 1, peptides with sequences corresponding to any one or more sequences in the Sequence Listing, homologous sequences to sequences described herein, and/or any other suitable sequences described herein (e.g., derivable from peptide sequence motifs described herein, etc.). In another example, the therapeutic composition can include one or more peptides derived from one or more microorganisms, and operable to bind to one or more TLRs (e.g., TLR2). In other examples, the therapeutic composition can include one or more peptides with sequences of any length and/or identity percentage to any of the sequences herein (e.g., including peptide sequences derivable from peptide sequence motifs described herein, such as including the residues in bold and maintaining each position pattern, etc.) but the therapeutic compositions can include peptides with any suitable percentage of identity and/or suitable substitution modifications.

In variations, peptides and/or other suitable components described herein can be encapsulated or covalently-conjugated with one or more carriers (e.g., of different composition, of same or similar composition, etc.), where carriers and/or components of the therapeutic composition can include any one or more of: micelles, polymers, liposomes, dendrimers, metallic nanoparticles, microspheres, polyelectrolyte complex, emulsions, hydrogels, and/or injectable polymers. In variations, peptides and/or other suitable components described herein can be conjugated or modified with different molecules.

The therapeutic compositions, method 100, and/or system 200 can function to modulate and/or bind to TLRs and/or other suitable proteins related to TLR-related conditions, in order to diagnose (e.g., the presence of, the severity of, etc.) and/or treat the TLR-related conditions in a patient. Additionally or alternatively, the therapeutic compositions, method 100, and/or system 200 can function to illuminate the roles of different types of microorganisms in specific health conditions (e.g., the role of *Akkermansia muciniphila* in diabetes and/or obesity), such as through identifying the modulating roles of peptides associated with the microorganisms. TLR-related conditions (e.g., directly and/or indirectly associated with TLRs such as TLR2, etc.) can include any one or more of: diabetes, obesity, sepsis, inflammatory disease (e.g., Crohn's disease), immune disorders, metabolic disease (e.g., conditions associated with metabolic syndrome), endocrine disease, atherosclerosis, asthma, cardiovascular disease, immune-related conditions, and/or any other suitable conditions. In examples, therapeutic compositions and/or components associated with the therapeutic compositions can inform interactions between microorganisms and TLR-related conditions (e.g., a protective role of *A. muciniphila* in a condition, etc.). Determination, generation, and/or delivery of the therapeutic compositions are preferably performable by the method 100 and/or system 200 described below, but can additionally or alternatively be performed through any suitable processes and/or components.

The components of the therapeutic composition and/or system 200 can be physically and/or logically integrated in any manner (e.g., with any suitable distributions of functionality across the components, such as in relation to portions of the method 100; etc.). Further, the therapeutic compositions, method 100, and system 200 can be configured in any manner analogous to U.S. application Ser. No. 15/098,027 filed 13 Apr. 2016 and entitled "Method and System for Microbiome-Derived Diagnostics and Therapeutics for Autoimmune System Conditions", and U.S. application Ser. No. 15/098,248 filed 13 Apr. 2016 and entitled "Method and System for Microbiome-Derived Diagnostics and Therapeutics for Endocrine System Conditions", each of which are herein incorporated in their entirety by this reference. However, the therapeutic compositions, method 100, and system 200 can be configured in any suitable manner.

2.1 Therapeutic Composition—Peptides

The one or more peptides of the therapeutic composition function to interact (e.g., bind as a ligand) with one or more TLR-related components (e.g., different types and/or regions of TLRs, such as a specific active site domain or section within the TLR receptor; TLR-related proteins; etc.) such as in order to modulate TLR-related functionality (e.g., TLR2 receptor signaling pathway) for diagnosing, detecting, treating and/or otherwise modulating one or more TLR-related conditions. TLRs can include any one or more of: TLR1, TLR2, TLR3, TLR4, TLR5, TLR6, TLR7, TLR8, TLR9, TLR10, TLR11, TLR12, TLR13, and/or other suitable TLRs expressed in humans, other mammals, and/or other organisms. In an example, the peptide can modulate TLR2-related functionality and/or can be derived based on reengineering of a target peptide sequence associated with a microorganism-related modulator of TLR2 (e.g., where the TLR-related condition can include at least one of a metabolic disease and an immune disorder, etc.). In a specific example, the therapeutic composition can include a peptide operable as an activator of TLR2 in improving one more of a metabolic disease and an immune disorder. In other examples, the peptide can be operable as an inhibitor of TLR2, but the peptides can include any one or more of: full agonists, agonists, antagonists, inverse agonists, allosteric modulators, and/or any suitable type of relationship with TLRs and/or any other suitable proteins. The peptides preferably influence immune system-related functionality of the TLRs, but can modulate and/or otherwise modify any suitable TLR-related functionality. In an example, the peptides can modulate protein-protein interactions with the TLR, such as between TLR2 and TLR1 and/or Toll interacting protein. In another example, the peptides can modulate protein-ligand interactions. The peptides can be used in in vivo and/or in vitro targeting of TLRs and/or TLR-related proteins, but can otherwise be configured.

The peptides are preferably associated with (e.g., characterized by, having, defining, etc.) one or more binding parameters including: binding energy (e.g., affinity energy), association rate, dissociation rate, half-life of interaction (e.g., between receptor and peptide), binding constants, binding specificity, thermodynamics associated parameters (e.g. enthalpy, entropy, Gibbs free energy), parameters associated with number and type of binding sites (e.g., stoichiometry), parameters associated with undesired binding (e.g., self-assembly, interference with other proteins, etc.), and/or any other suitable binding parameters. The binding parameter values for the peptides (e.g., in relation to binding with TLRs) are preferably at least comparable to or improved over wild types peptides associated with microorganisms, but the binding parameters can have any suitable values. In an example, the therapeutic composition can include a peptide with a binding energy that is at least 1 Kcal/mol lower than wild type peptides, that implies a more favorable affinity between ligand and receptor. In another example, the therapeutic composition can include a peptide with a binding energy to TLR2 that is lower (e.g., a more favorable affinity) than a native peptide derived from Amuc_1100, a protein from *Akkermansia muciniphila* (*A. muciniphila*) and a putative activator of TLR2. In specific examples, the peptides can display TLR2 binding energies described in Table 1 below, where the binding energies are lower (e.g., a more favorable affinity) than a binding energy associated with a native peptide derived from Amuc_1100 (e.g., −6.8 Kcal/mol for a peptide sequence of LGFELK (SEQ ID NO:37736), etc.). Additionally or alternatively, the peptides can have comparable and/or improved binding parameters in relation to those associated with any suitable TLR-binding ligand, such as TLR2-binding ligands including any one or more of: MALP-2, MALP-404, OspA, antigen mixtures, lipomannan, LcrV, Porin, GPI anchor, hemagglutinin, zymosan, glycophosphatidylinositol, lipophosphoglycan, lysophosphatidylserine, glycolipids, lipopeptides, HSP60, HSP70, zymosan, lipoteichoic acid, lipoproteins, and/or other suitable modulators. However, these molecules can be also associated with any suitable parameters describing the characteristics of the peptides.

The peptides preferably possess peptide sequences derivable from peptide sequence motifs, such as including one or more of: nXXGFXLKXXn (SEQ ID NO:1), nXXTPA[ND][NE]XXXn (SEQ ID NOS:2-5), n[X][Z][B]APWn (SEQ ID NOS:6-245), nPP[X][Z][B][O]Pn (SEQ ID NOS:246-693), n[X][Z][i][O][B][J][f]n (SEQ ID NOS:694-35253), n[X][J]TAYKP[B]n (SEQ ID NOS:35304-35323), n[X]A[J][B]AP[Z]I[O][U]n (SEQ ID NOS:35324-35803), n1-1[X][J]QP[B]AQEPn (SEQ ID NOS:35804-35839), n[B]AR[X]TP[Z]SPPn (SEQ ID NOS:35284-35303), nF[X]PPAP[J]n (SEQ ID NOS:35254-35269), nDFT[X]FPPn (SEQ ID NOS:35270-35271), and n[X]TPA[J]F[B]n (SEQ ID NOS:35272-35283), where the notation is described above in Section 1, and where "n" can correspond to any number and type of amino acids (e.g., including n=0). Additionally or alternatively, the peptide sequences can be derivable from any homologous peptide sequence motifs (e.g., varying in sequence length, number and/or positioning of unspecified Xaa amino acids, additional or alternative amino acids, and/or with respect to any other suitable aspect of the peptide sequence motifs, etc.). Additionally or alternatively, the peptide sequence motifs can be determined based on applying substitution, deletion, insertion, duplication, inversion, and/or any other suitable operations. For example, the peptide sequence motifs can include xGFXLK (SEQ ID NO:1)(e.g., where the notation is described above in Section 1), which can be determined based on performing suitable operations on the XXGFXLKXX (SEQ ID NO:1) peptide sequence motif. In specific examples, the xGFXLK (SEQ ID NO:1) peptide sequence motif can be used in determining the peptide sequences described in Table 1 below, and/or any other suitable peptide sequences. Additionally or alternatively, such operations can be applied to any suitable peptide sequence motifs and/or peptide sequences described herein. In a variation, the unspecified Xaa amino acids and/or residues at other suitable positions in the peptide sequence motifs can be any amino acid type with equal probability. In another variation, the amino acid types for the unspecified Xaa amino acids and/or residues at other suitable positions can be characterized by unequal probabilities (e.g., with higher or lower probabilities based on the amino acid properties including hydrophobicity, polarity, dissociation constants, association constants, molecular weight, residue weight, pH, molecular formula and/or other suitable properties, such as in relation to correlation with binding parameters associated with TLRs). In another variation, Xaa can indicate no amino acid. However, the therapeutic composition can include peptides derived from any suitable peptide sequence motifs (e.g., including any suitable amino acids described in Table 12 below and/or other amino acid forms, etc.).

The peptide sequences are preferably derived from (e.g., are modifications of, variants of, etc.) modulators of TLRs and/or TLR-related proteins. Modulators of TLRs and/or TLR-related proteins can be associated with human-origin, microbial origin, and/or any other suitable origin. Modulators can be known modulators, putative modulators, unknown modulators, identified modulators, and/or any other suitable type of modulators. In a variation, the peptide sequence motifs can be derived from peptides of microbial origin. In a specific example, the xGFXLK (SEQ ID NO:1) peptide sequence motif can be extracted from the peptide sequence of LGFELK (SEQ ID NO:37736) in a native peptide of the Amuc_1100 protein of *A. muciniphila*, where the bolded letters indicate the amino acids conserved between the native peptide sequence and the peptide sequence motif. In this specific example, the xGFXLK (SEQ ID NO:1) peptide sequence motif can be used in determining peptide sequences including any one or more of: FGFELK; YGFELK; WGFELK; IGFELK; LGFHLK; LGFFLK; LGFFLK; LGFQLK; LGFGLK; LGFPLK; LGFSLK; LGFVLK; LGFRLK; LGFCLK; LGFTLK; LGFWLK; and LGFYLK (SEQ ID NOS:37719-37735, respectively), where the italicized letters indicate amino acids that have been mutated from the native peptide sequence. In another specific example, peptide sequence motifs and/or other suitable aspects associated with components of therapeutic compositions can be derived from Amuc_1100 and/or other molecules associated with *A. muciniphila* and/or other suitable microorganisms of other suitable taxonomic groups with positive or inverse correlations with conditions (e.g., diabetes such as type 2 diabetes, obesity, autoimmune conditions, etc.). In another specific example, the peptides can be derived based on reengineering of the target peptide sequence associated with a microorganism-related modulator associated with Amuc_1100 protein (e.g., peptide sequence segments from the Amuc_1100 amino acid sequence, etc.) from *Akkermansia muciniphila*, and where the peptides can correspond to one or more peptide sequences derivable from at least one of nXXGFXLKXXn (SEQ ID NO:1), nXXTPA[ND][NE]XXXn (SEQ ID NOS: 2-5), n[X][Z][B]APWn (SEQ ID NOS:6-245), nPP[X][Z][B][O]Pn (SEQ ID NOS:246-693), n[X][Z][i][O][B][J][f]n (SEQ ID NOS:694-35253), n[X][J]TAYKP[B]n (SEQ ID NOS:35304-35323), n[X]A[J][B]AP[Z]I[O][U]n (SEQ ID NOS:35324-35803), and nH[X][J]QP[B]AQEPn (SEQ ID NOS:35804-35839). In another specific example, peptide sequence motifs and/or other suitable aspects associated with components of therapeutic compositions can be derived from Rv1168c protein from *Mycobacterium tuberculosis* (e.g., associated with HIV trans-activation through activation of TLR2 receptor). In another specific example, the peptides can be derived based on reengineering of the target peptide sequence associated with a microorganism-related modulator associated with Rv1168c protein (e.g., peptide sequence segments from the Rv1168c amino acid sequence, etc.) from *Mycobacterium tuberculosis*, and where the peptides can correspond to one or more peptide sequences derivable from at least one of n[B]AR[X]TP[Z]SPPn (SEQ ID NOS:35284-35303), nF[X]PPAP[J]n (SEQ ID NOS: 35254-35269), nDFT[X]FPPn (SEQ ID NOS:35270-35271), and n[X]TPA[J]F[B]n (SEQ ID NOS:35272-35283). In another variation, the peptide sequence motifs can be derived from peptides of human-origin (e.g., described in databases including but not limited to Peptide-Atlas, Proteomics DB, Signal Peptide Database, Pepbank, etc.), and/or from peptides of human-origin and microbial-origin (e.g., determining a peptide sequence motif based on combining aspects of a human-origin peptide with aspects of a microbial-origin peptide, etc.). Additionally or alternatively, peptide sequence motifs and/or peptide sequences can be derived based on reengineering of target peptide sequences (e.g., mutating amino acid residues of the target peptide sequences, such as modifying amino acid residues, adding amino acid residues, deleting amino acid residues, in any suitable position, etc.) associated with microorganism-related modulators (e.g., associated with Amuc_1100, such as where one or more target peptide sequences are from the Amuc_1100 amino acid sequence; associated with Rv1168c; etc.). In examples, the peptide sequence motifs and/or peptide sequences can be based on binding parameter values for TLR binding site (and/or other suitable binding sites) for one or more molecules, such as Staphylococcal Superantigen-Like protein 3 (SSL3) (e.g., where the peptide is associated with Amuc_1100 and derivable from at least one of n[X][Z][B]APWn (SEQ ID NOS:6-245), nPP[X][Z][B][O]Pn (SEQ ID NOS:246-693), n[X][Z][i][O][B][J][f]n (SEQ ID NOS:694-35253); where the peptide is associated with Rv1168c and derivable from at least one of nF[X]PPAP[J]n (SEQ ID NOS:35254-35269), nDFT[X]FPPn (SEQ ID NOS:35270-35271), n[X]TPA[J]F[B]n (SEQ ID NOS: 35272-35283); etc.), a proline-proline glutamic acid protein (e.g., where the peptide is associated with Amuc_1100 and derivable from at least one of n[X][J]TAYKP[B]n (SEQ ID NOS:35304-35323), n[X]A[J][B]AP[Z]I[O][U]n (SEQ ID NOS:35324-35803), nH[X][J]QP[B]AQEPn (SEQ ID NOS: 35804-35839); where the peptide is associated with Rv1168c and derivable from at least one of n[B]AR[X]TP[Z]SPPn (SEQ ID NOS:35284-35303); etc.) and/or other suitable proteins and/or molecules. Additionally or alternatively, peptide sequence motifs can be derived independently of modulators, such as through in silico techniques (e.g., models) applying algorithms including random properties. However, peptide sequence motifs can be derived from modulators in any suitable manner.

The therapeutic composition can include peptides possessing specific amino acid pattern sequences with any suitable degree of identity (e.g., at least 50%, 70%, 90%, single amino acid, multiple amino acids, etc.) to the peptide sequences and/or peptide sequence motifs described herein. In a specific example, the therapeutic composition can include one or more peptides corresponding to one or more peptide sequences with at least 90% identity to one or more determined peptide sequences derivable from at least one peptide sequence motif described herein and/or other suitable peptide sequences described herein (e.g., described in the Sequence Listing, etc.). The identity between peptide sequences and/or peptide sequence motifs can be represented at any suitable positions in the sequences (e.g., the identity can be achieved through contiguous amino acids and/or non-contiguous amino acids in the sequences, etc.). However, identity between peptide sequences and/or peptide sequence motifs can be configured in any suitable manner.

Peptide sequences and/or peptide sequence motifs can possess any suitable length (e.g., number of amino acids in the sequence). In a specific example, the therapeutic composition can include a hexapeptide selected from Table 1. In another specific example, at least two amino acids can be inserted upstream (e.g., amino end) and at least two amino acids can be inserted downstream (e.g., carboxylic end) of a peptide sequence (e.g., for a modulator) and/or peptide sequence motif (e.g., derived from a modulator), but any suitable number of amino acids can be inserted and/or deleted from sequences described herein.

The therapeutic compositions can include any number of peptides possessing any number of peptide sequences derived from any number of peptide sequence motifs. In a specific example, the therapeutic composition can include peptides derived from a combination of peptide sequence motifs, where combination of peptides can include one or more of: combining two or more peptides together into a therapeutic composition for diagnostics purpose, combining two or more peptides into one single peptide that maintains both sequence motifs for each peptide combined in one molecule, and/or any other suitable combination of peptide sequence motifs and/or peptide sequences derivable from peptide sequence motifs described herein (e.g., a combination between a first peptide sequence motif described herein and a second peptide sequence motif with at least 2 amino acids inserted upstream at an amino end and at least 2 amino acids inserted downstream at an carboxylic end, etc.). In a specific example, the peptide can correspond to a peptide sequence derivable from nXX[MOTIF1][α][α]NS[α][α]N[β]LA[γ]C[AG]LS[62][δ]I[β]V[δ][β][δ]QL[δ]I[γ][MOTIF2]X Xn (SEQ ID NOS:35840-35983), where α includes an aromatic type amino acid selected from at least one of F, W and T, where β includes a positive type amino acid selected from at least one of R, H and K, where γ includes a negative type amino acid selected from at least one of D and E, where δ includes any amino acid, except for α, β and γ types, where X includes any amino acid type or no amino acid, where n includes any number and type of amino acid, where MOTIF1 includes a first target motif from a set of peptide sequence motifs including peptide sequence motifs described herein, and where MOTIF2 includes a second target motif (e.g., different from the first target motif, same as the first target motif, etc.) from the set of peptide sequence motifs. In another specific example, the peptide can correspond to a peptide sequence derivable from a combination of at least three motifs (e.g., different motifs, same motifs, etc.) from a set of peptide sequence motifs including peptide sequence motifs described herein, where the peptide corresponds to the peptide sequence derivable from nXX[MOTIF1]nX[MOTIF2]nX[MOTIF3]XXn (SEQ ID NOS: 35984-37711), where X includes any amino acid type or no amino acid, and where n includes any number and type of amino acid.

However, peptides and/or other suitable molecules included in one or more therapeutics composition can be configured in any suitable manner.

TABLE 1

Example Peptide Sequences and Associated Binding Energies on TLR2.

| Sequence | Binding Energy |
|---|---|
| FGFELK (SEQ ID NO: 37718) | -7.5 Kcal/mol |
| YGFELK (SEQ ID NO: 37719) | -7.3 Kcal/mol |
| WGFELK (SEQ ID NO: 37720) | -7.2 Kcal/mol |
| IGFELK (SEQ ID NO: 37721) | -7.0 Kcal/mol |
| LGFHLK (SEQ ID NO: 37722) | -7.2 Kcal/mol |
| LGFFLK (SEQ ID NO: 37723) | -7.2 Kcal/mol |
| LGFNLK (SEQ ID NO: 37724) | -7.1 Kcal/mol |
| LGFQLK (SEQ ID NO: 37725) | -7.0 Kcal/mol |
| LGFGLK (SEQ ID NO: 37726) | -7.0 Kcal/mol |
| LGFPLK (SEQ ID NO: 37727) | -7.0 Kcal/mol |
| LGFSLK (SEQ ID NO: 37728) | -7.0 Kcal/mol |
| LGFVLK (SEQ ID NO: 37729) | -7.0 Kcal/mol |
| LGFRLK (SEQ ID NO: 37730) | -6.9 Kcal/mol |
| LGFCLK (SEQ ID NO: 37731) | -6.9 Kcal/mol |
| LGFTLK (SEQ ID NO: 37732) | -6.9 Kcal/mol |
| LGFWLK (SEQ ID NO: 37733) | -6.9 Kcal/mol |
| LGFYLK (SEQ ID NO: 37734) | -6.9 Kcal/mol |

2.2 Therapeutic Composition—Microorganisms

The therapeutic composition can additionally or alternatively include any ligands and/or other biomolecules derived from microorganisms corresponding to taxonomic groups associated with TLRs, where the ligands and/or other biomolecules can function to facilitate interactions between the peptides of the therapeutic composition and TLRs and/or TLR-related proteins in order to facilitate diagnosis and/or treatment of TLR-related conditions. Additionally or alternatively, the therapeutic composition can include the microorganisms themselves (e.g., in a therapeutic composition including probiotics, etc.). In a variation, the therapeutic composition can include biomolecules derived from microorganisms expressing and/or encoding genes homologous to genes encoding Amuc_1100 and/or similar proteins (e.g., in relation to amino acid sequence, functionality, etc.), such as those including peptide sequences that are similar to (e.g., with an identity greater than an identity threshold), the same as, and/or derivable from the peptide sequences and/or peptide sequence motifs described herein. In another variation, the therapeutic composition can include microorganism-derived biomolecules facilitating the modulation of TLRs and/or TLR-related proteins by the peptides (e.g., biomolecules supporting binding and/or other suitable interactions between the peptides and the TLRs, etc.), where the biomolecules can be derived from microorganisms of the same or different type as those associated with the corresponding peptide in the therapeutic composition. In other variations, the therapeutic composition can include peptides and/or other biomolecules associated with (e.g., derived from associated peptide sequences) one or more types of microorganisms (e.g., the therapeutic composition including peptides derived based on reengineering of one or more target peptide sequences associated with one or more microorganism-related modulators associated with at least one of the following set of taxa, etc.) including at least one of: *A. muciniphila, Mycobacterium tuberculosis (M. tuberculosis), Faecalibacterium prausnitzii, Lactobacillus rhamnosus, Bacteroides fragilis, Porphyromonas gingivalis, Leptospira, Chlamydophila pneumoniae, Borrelia burgdorferi, Neisseria meningitidis, Haemophilus influenzae, Yersinia, Schistosoma mansoni, Trypanosoma cruzi, Mycobacterium, Propionibacterium acnes, Mycoplasma, Aspergillus fumigatus, Candida albicans, Malassezia, Saccharomyces cerevisiae, Plasmodium falciparum, Leishmania major,* Planctomycetes-Verrucomicrobia-Chlamydiae, Firmicutes, Bacteroidetes, gram-positive bacteria, herpes simplex virus, cytomegalovirus, varicella zoster virus, measles, fungi, archaea, gram-negative bacteria, virus, phages and/or any other suitable types of microorganisms across different groups of kingdoms, phyla, classes, orders, families, genera, species, subspecies, strains, infraspecies taxon, and/or any other suitable taxa (e.g. associated with a TLR). In variations, the therapeutic composition can include peptides and/or other biomolecules associated with microorganisms from taxonomic groups and/or with functionality described in U.S. application Ser. No. 15/098,027 filed 13 Apr. 2016 and entitled "Method and System for Microbiome-Derived Diagnostics and Therapeutics for Autoimmune System Conditions", and U.S. application Ser. No. 15/098,248 filed 13 Apr. 2016 and entitled "Method and System for Microbiome-Derived Diagnostics and Therapeutics for Endocrine System Conditions", each of which are herein incorporated in their entirety by this reference. However, ligands and/or other biomolecules derived from any suitable types of microorganisms can be included in the therapeutic composition and can be configured in any suitable manner.

2.3 Therapeutic Composition—Other

The therapeutic composition and/or components (e.g., peptides, other biomolecules) of the therapeutic composition can be in any suitable form suitable for facilitating delivery and/or treatment for one or more patients. The peptides in the therapeutic composition are preferably in a purified and/or isolated form, achieved through any suitable sample handling operation including one or more of: chromatography (e.g., size exclusion chromatography; high performance liquid chromatography; chromatography based on hydrophobicity; affinity chromatography; etc.), desalting, washing, centrifuging, and/or any suitable operation; however, the peptides can be in any suitable form. Additionally or alternatively, the therapeutic composition can include any one or more of: a pharmaceutical carrier, a lipid carrier, a dendrimeric carrier, a polymeric carrier, a metallic nanoparticle carrier, an amphiphilic carrier (e.g., composed by hydrophilic and hydrophobic sections), micelles, liposomes, an aqueous medium (e.g., water, oils, glycerol, glycol, ethanol, polyols, etc.), anti-angiogenic agents, therapeutic agents (e.g., chemotherapeutic agents), antimetabolites, natural compounds, alkylating agents, and/or any other suitable carriers and/or agents for facilitating diagnosis and/or treatment of TLR-related conditions, and can be administered by oral way, parenteral way, by osmotic pumps, and/or any other suitable manner. In examples, peptides and/or other suitable components described herein can be encapsulated or covalently-conjugated with one or more carriers (e.g., of different composition, of same or similar composition, etc.), where carriers and/or components of the therapeutic composition can include any one or more of: micelles, polymers, liposomes, dendrimers, metallic nanoparticles, microspheres, polyelectrolyte complex, emulsions, hydrogels, and/or injectable polymers.

In variations, peptides and/or other suitable components described herein can be conjugated or modified with different molecules (e.g., to increase their stability, to help to reach one or more targets, to prevent degradation such as in an extracellular environment, etc.). For example, peptides can be modified with non-natural amino acids (e.g., to prevent hydrolytic enzymes and/or proteases that can recognize them and can break peptide linkages, etc.). In examples, stereochemical modification, peptide bond surrogates, and/or other techniques can be applied. In examples, techniques promoting conformational stabilization can be applied (e.g., backbone cyclization, stapled peptides, disulfide formation, polymerization, tertiary structure formation, etc.) and/or shielding strategies can be applied (e.g., self-assembling, polymer conjugation, controlled shielding, etc.). Techniques and/or other suitable approaches described herein can improve upon potential characteristics of peptides (e.g., low hydrolytic stability in presence of enzymes; aggressiveness of biological fluids for peptides due to presence of proteases and peptidases; degradation in incubation in serum-containing media; etc.).

However, therapeutic compositions can include any suitable components configured in any suitable manner, and any suitable techniques can be applied in improving characteristics of components of the therapeutic compositions.

3. Method

Figure 3:
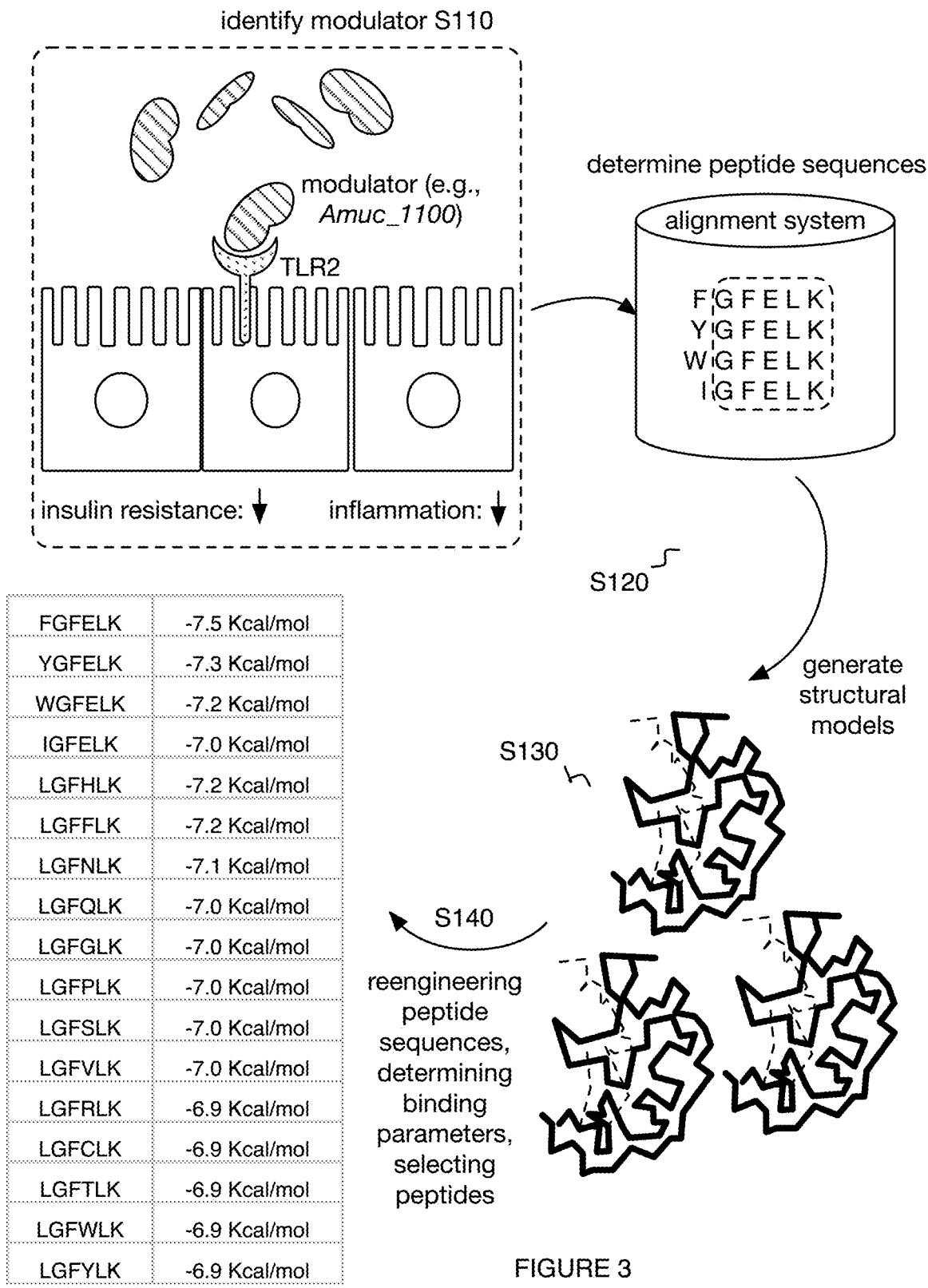
FIG. 3 is a schematic representation of variations of embodiments of therapeutic compositions and a method for facilitating diagnosis and/or treatment of a condition (determine peptide sequences=SEQ ID NOS:37719-37721, respectively; peptides selected=SEQ ID NOS:37719-37735).

As shown in FIGS. 1-3, embodiments of a method 100 for improving a TLR-related condition (e.g., through determining peptide sequences operable to facilitate modulation, diagnosis, detection, and/or treatment of a TLR-related condition in a patient, etc.) can include: identifying a modulator of at least one of a TLR and a TLR-related protein (e.g., based on an analysis of biomolecules associated with microbial-origin and/or other suitable origin, etc.) S110; determining one or more peptide sequences (e.g., a set of peptide sequences, etc.) associated with the modulator (e.g., a microorganism-related modulator, etc.), such as peptide sequences with an identity satisfying an identity threshold (e.g., at least 50%, 70%, 90%, single amino acid, multiple amino acids, etc.) to the modulator S120; determining a set of binding parameters for the set of peptide sequences in relation to the TLR S130; and/or determining a therapeutic composition based on the set of binding parameters S140. In variations, determining a therapeutic composition S140 can additionally or alternatively include selecting a target subset of peptide sequences from the one or more peptide sequences based on the first set of binding parameters; reengineering the target subset of peptide sequences (e.g., based on mutating amino acid residues, such as through modifying amino acid residues, adding amino acid residues, deleting amino acid residues, at any suitable position, etc.); determining a second set of binding parameters for the reengineered target subset of peptide sequences in relation to the TLR; and/or identifying one or more peptides and/or other suitable molecules for use in one or more therapeutic compositions for improving the TLR-related condition, based on the second set of binding parameters for the reengineered target subset of peptide sequences (e.g., through selecting peptide sequences based on higher binding affinity for the receptor, i.e., lower free energy). In an example, a first peptide, a second peptide, and/or any suitable number of peptides can be identified for use in the therapeutic composition, such as based on the second set of binding parameters, where the first peptide can correspond to a first peptide sequence different from a second peptide sequence corresponding to the second peptide. Embodiments of the method 100 can additionally or alternatively include delivering the therapeutic composition to a patient (e.g., in a form described in Section 2) in order to improve the TLR-related condition S150; and/or any other suitable operations.

In variants, any suitable Blocks of the method 100 can be repeatedly performed in any suitable order (e.g., in a cycle, as shown in FIG. 1), such as to refine a therapeutic composition (e.g., based on reengineering peptides based on mutating amino acids, including mutating non-conserved amino acids, such as through modifying, adding, and/or deleting amino acid residues) and/or to generate a plurality of therapeutic compositions (e.g., including different reengineered peptides). In an example, the method 100 can include refining the therapeutic composition, where refining the therapeutic composition includes selecting a second target subset of peptide sequences from a second set of peptide sequences based on a third set of binding parameters (e.g., in relation to the TLR associated with the first and/or second set of binding parameters; in relation to a different TLR; etc.); reengineering the second target subset of peptide sequences; determining a fourth set of binding parameters for the reengineered second target subset of peptide sequences (e.g., in relation to the TLR associated with the first and/or second set of binding parameters; in relation to a different TLR; etc.); and/or identifying a second peptide for use in the refined therapeutic composition for improving the TLR-related condition, based on the fourth set of binding parameters. However, any suitable Blocks of the method 100 can be repeated in any suitable sequence for any suitable purpose.

One or more instances of the method 100 and/or processes described herein can be performed asynchronously (e.g., sequentially), concurrently (e.g., in parallel; concurrently on different threads for parallel computing to improve system processing ability for determining peptide sequences; etc.), in temporal relation to a trigger event, and/or in any other suitable order at any suitable time and frequency to determine one or more peptide sequences and/or peptide sequence motifs described herein, such as through using one or more instances of the system 200 (e.g., including a sample handling network, a peptide sequence determination system such as a remote computing system and/or other suitable system components for determining peptide sequences and/or peptide sequence motifs, etc.). In variations, the method 100, system 200, and/or therapeutic compositions can include any aspects analogous to those described in U.S. application Ser. No. 14/593,424 filed 9 Jan. 2015 and entitled "Method and System for Microbiome Analysis", and U.S. application Ser. No. 14/919,614 filed 21 Oct. 2015 and entitled "Method and System for Microbiome-Derived Diagnostics and Therapeutics", each of which are herein incorporated in their entirety by this reference. However, the method 100 and system 200 can be configured in any suitable manner to facilitate peptide sequence determination.

3.1 Method—Identifying a Modulator.

Block S110 recites: identifying a modulator of at least one TLR-related component (e.g., a TLR and/or a TLR-related protein, etc.), such as based on an analysis of biomolecules associated with microbial-origin and/or other suitable origin. Block S110 can function to select putative modulators that can be analyzed to determine peptide sequences associated with modulation of target functionality (e.g., functionality corresponding to TLRs and TLR-related proteins). In a specific example, Block S110 can include identifying Amuc_1100 protein associated with *A. muciniphila*, Rv1168c protein associated with *M. tuberculosis*, and/or other suitable modulators of TLR-related proteins. Identifying modulators can be based on: sequencing (e.g., performing microbiome sequencing to identify genes encoding proteins associated with TLR modulation for populations of patients with or without TLR-related conditions; performing protein sequencing on microbial-derived ligands binding to TLRs; etc.), scientific literature (e.g., performing natural language processing on scientific literature associated with TLR2 modulation to identify modulators, etc.), peptide databases (e.g., generating a plurality of API requests tailored to different peptide databases; applying machine learning algorithms to identify and select modulators; etc.), and/or any suitable aspect.

In a variation, Block S110 can include identifying one or more regions of one or more modulators, which can function to identify regions (e.g., regions including sequences of interest, such as based on binding energy and/or other suitable characteristics, etc.) from which peptide sequences can be derived (e.g., in Block S120). In a specific example, the cytoplasmic and/or extracellular regions of Amuc_1100 and/or other suitable modulators can be identified (e.g., stored at a remote server for subsequent analysis, etc.). In another specific example, the N-terminal region of a proline-proline glutamic acid protein type (e.g., Rv1168c, etc.) can be identified. However, any suitable regions and/or other suitable aspects of modulators can be determined and/or otherwise utilized for deriving therapeutic compositions.

Block S110 is preferably performed at a peptide sequence determination system, which can include one or more of: a remote computing system (e.g., a server, at least one networked computing system, stateless, stateful), a local computing system, a user device (e.g., user smartphone, laptop, tablet, computing system, etc.), databases (e.g., peptide databases, microorganism databases, etc.), and/or any suitable component. Additionally or alternatively, identifying a modulator can be performed at a sample handling network (e.g., through in vivo experiments for determining modulation functionality of peptides, evaluation of physiological effect after using therapy composition, etc.), which can include one or more of: peptide analysis systems (e.g., a phage display system, a mass spectrometry system, etc.), a sequencing system (e.g., protein sequencing system; microbiome sequencing system; etc.), a library preparation system, sample kits (e.g., including sample containers, associated instructions), and/or any other suitable sample handling components. However, Block S110 can be performed by any suitable component in any suitable manner.

3.2 Method—Determining One or More Peptide Sequences

Block 120 recites: determining one or more peptide sequences (e.g., a set of peptide sequences, etc.) associated with the modulator (e.g., a microorganism-related modulator, etc.), such as with an identity satisfying an identity threshold for the modulator, which can function to identify a pool of peptide sequences with potential TLR-modulation functionality. The degree of identity can be based on peptide sequence motifs (e.g., a degree of identity corresponding to the number of Xaa amino acids in the peptide sequence motif, etc.) extracted from peptide sequences corresponding to modulators, but can additionally or alternatively be based on any suitable parameters (e.g., functional considerations, therapeutic considerations, etc.). Determining the set of peptide sequences can include one or more of: performing alignment operations (e.g., local alignments using BLAST tools, FASTA algorithm) with a set of alignment parameters (e.g., length parameters, such as to limit identification to peptides of short length with >4 amino acids; scoring parameters; gap penalty parameters; E-value; percent identity; percent similarity; etc.); extracting peptide sequence motifs; and/or any other suitable operation. In a specific example, Block S120 can include performing a local alignment operation on peptide sequences derived from the Amuc_1100 of *A. muciniphila*. Block S120 is preferably performed at the peptide sequence determination system but can additionally or alternatively be performed at any suitable component.

In a variation, Block S120 can include determining a set (e.g., a library, a plurality, etc.) of peptide sequences (and/or the peptides characterized by the peptide sequences, etc.) associated with different sequence lengths (e.g., 6-10 amino acids, any suitable sequence length, etc.), such as based on cytoplasmic and extracellular regions of the Amuc_1100 protein. However, Block S120 can be performed in any suitable manner.

3.3 Method—Determining Binding Parameters.

Block S130 recites: determining binding parameters (e.g., types of which are described above in Section 2) for the set of peptide sequences and/or peptides derived from the peptide sequences (e.g., such as binding parameters in relation to binding with TLR, etc.), which can function to evaluate the peptide sequences for diagnosis and/or treatment purposes. Determining binding parameters preferably includes generating structural models in silico (e.g., through in silico techniques) for the set of peptide sequences. In a specific example, Block S130 can include determining structural models in silico (e.g., at a peptide sequence determination system) for peptide sequences derived from mutating the variable Xaa positions in the xGFXLK (SEQ ID NO:1) peptide sequence motif; and performing free energy calculations using molecular simulations with the structural models to determine binding energies on TLR2 (e.g., described in Table 1). Block S130 (and/or other suitable portions of the method 100, such as determining binding parameters for reengineered peptide sequences, etc.) can include determining binding parameters with one or more techniques (e.g., in silico techniques, etc.) including one or more of: a molecular docking technique, a MM-(GB/PB)SA (Molecular Mechanics (Generalized Born/Poisson-Boltzmann) Surface Area) technique, free energy perturbation (FEP) technique, an adaptive biasing force (ABF) technique, an umbrella sampling method technique, and/or other suitable techniques. Additionally or alternatively, determining binding parameters can be performed with systems (e.g., the sample handling network) operable to determine binding parameters through in vitro processes (e.g., phage display; mass spectrometry; isothermal microcalorimetry, calorimetry, fluorescence binding assays, high throughput peptide analysis; etc.), in vivo processes, and/or any suitable processes.

In a variation, Block S130 can include applying molecular docking techniques to determine the relative energy of binding (and/or other suitable binding parameters) between one or more TLRs (e.g., TLR2, etc.) and one or more sets of peptides (e.g., characterized by peptide sequences determined in Block S120, etc.). In an example, Block S130 can include identifying one or more sites (e.g., known sites, putative sites, unknown sites, identified sites, etc.) of one or more TLRs for evaluating binding parameters (e.g., using molecular docking techniques and/or other suitable techniques, etc.). In a specific example, Block S130 can include identifying a first site as a TLR2 binding site of SSL3 associated with (e.g., from, etc.) *Staphylococcus aureus* (e.g., crystallized and/or deposited in the Protein Data Bank, etc.), and/or identifying a second site as a TLR2 binding site of a proline-proline glutamic acid protein (e.g., Rv1168c) associated with *Mycobacterium tuberculosis*, where the first site can correspond to leucine-rich repeats (LRR) 11-13 and/or the second site can correspond to LRR 15-19 in TLR2 receptor. Additionally or alternatively, any suitable sites of any suitable TLRs and/or other suitable molecules can be identified and/or associated with any suitable microorganisms. Sites can be defined as the center of a grid (e.g., 33 Å$^3$ in size, etc.), and/or any suitable location and/or shape for use in molecular docking techniques and/or other suitable techniques.

However, Block S130 and other portions of the method 100 can be performed in any suitable manner (e.g., determining other suitable parameters in evaluating identified peptide sequences, etc.).

3.4 Method—Determining a Therapeutic Composition.

Block S140 recites: determining a therapeutic composition, which can function to determine one or more components of one or more therapeutic compositions associated with one or more TLRs. Block S140 can include determining any suitable component suitable for a therapeutic composition, such as any one or more of peptide sequences, motifs, forms for delivery, carriers, agents, supplemental components, generation protocols, and/or other suitable components.

In a variation, Block S140 can include reengineering (e.g., mutating, substituting amino acids, etc.) peptide sequences and/or peptides derived from the peptide sequences S142. As such, Block S140 can include determining a target set of peptide sequences and/or peptides to reengineer, such as based on binding parameters (e.g., determined in Block S130), and/or any other suitable parameters. The target set of peptide sequences and/or peptides can be the same as the set of peptide sequences determined in Block S120, a subset of the set of peptide sequences (e.g., peptide sequences of modulators corresponding to binding sites at TLR-related proteins, peptide sequences with binding parameter performance satisfying a threshold condition, peptide sequences with binding energy satisfying a threshold condition, peptide sequences selected based on a ranking of binding parameter performance, etc.), and/or can include any suitable peptide sequences and/or peptides. As such, Block S140 can additionally or alternatively include selecting a target subset of peptide sequences (e.g., for performing subsequent analyses, such as reengineering and/or additional binding parameter determination, etc.) from a set of peptide sequences based on binding parameters (e.g., binding parameters determined in Block S130).

Reengineering can include mutating amino acids at any suitable position of the target peptide sequences and/or peptides (e.g., modifying amino acid residues, adding amino acid residues, deleting amino acid residues, etc.). Mutating can include mutation of any suitable amino acid to any other suitable amino acid. In an example, Block S140 can include reengineering (e.g., mutating, with other amino acid residues, at each position of each peptide sequence, etc.) and/or peptide at a first target set of peptide sequences and/or peptides derived from Amuc_1100 (e.g., target peptide sequences associated with Amuc_1100) and targeting a first site of a first TLR-related protein (e.g., TLR2 binding site for SSL from *Staphylococcus aureus*); reengineering a second target set of peptide sequences and/or peptides derived from Rv1168c (e.g., target peptide sequences associated with Rv1168c) and targeting the first site; reengineering a third target set of peptide sequences and/or peptides derived from Rv1168c and targeting a second site of the same or different TLR-related protein (e.g., TLR2 binding site for a proline-proline glutamic acid protein such as Rv1168c from *Mycobacterium tuberculosis*); and/or reengineering a fourth target set of peptide sequences and/or peptides derived from Amuc_1100 and targeting the second site. Block S140 can additionally or alternatively include determining binding parameters for the reengineered peptide sequences (e.g., for peptides derivable from the peptide sequences). For example, molecular docking runs and/or other suitable techniques can be performed on the first, second, third, fourth, and/or other suitable target peptide sequences and/or peptides, and optimization parameters (e.g., ranking based on binding parameter values, such as based on binding parameter values that was best performing out of a plurality of molecular docking runs, etc.) can be applied for determining a select set of peptide sequences and/or peptides (e.g., selecting the peptide sequences and/or peptides with equal to or less than the relative energy of binding than one or more wild peptide sequences and/or peptides, etc.), such as for identifying one or more peptides for use in the therapeutic composition based on the binding parameters (e.g., identifying peptide sequence motifs based on performance rankings of the binding parameters, and identifying peptides derivable from the peptide sequence motifs, etc.). However, reengineering peptide sequences and/or determining associated binding parameters can be performed in any suitable manner.

In the example, the first target set of peptide sequences and/or peptides (e.g., derived from Amuc_1100 and targeting the first site, etc.) can additionally or alternatively include (e.g., based on best performing affinity to the first site, etc.) ADQAPW (SEQ ID NO:198) (e.g., −9.6 kcal/mol), PPPIANP (SEQ ID NO:693) (e.g., −10.3 kcal/mol) and WLGFQVY (SEQ ID NO:35253) (e.g., −9.7 kcal/mol), where reengineering the first target set can result in binding energies (e.g., derived from molecular docking results, etc.) shown in Tables 2, 3, and 4. Describing Tables 2-11, the first row of each table depicts the position of each amino acid in the corresponding target peptide and/or peptide sequence, and the first column corresponds to the 20 naturally occurring amino acids. Describing Table 2, residue 1 (ALA1) from the native peptide ADQAPW (SEQ ID NO:198) may be mutated by PHE, resulting in a new reengineered peptide FDQAPW (SEQ ID NO:54) that binds the TLR2 receptor with a better-performing affinity (−10.1 kcal/mol) than the native peptide (−9.6 kcal/mol).

TABLE 2

Mutants of ADQAPW (SEQ ID NO: 198) peptide (in kcal/mol)

| | ALA1 | ASP2 | GLN3 | ALA4 | PRO5 | TRP6 |
|---|---|---|---|---|---|---|
| ALA | | −10 | | | | |
| ARG | | | | | | |
| ASN | | | | | | |
| ASP | | | | | | |
| CYS | | | | | | |
| GLN | | −9.9 | | | | |
| GLU | | −9.7 | | | | |
| GLY | | −9.8 | | | | |
| HIS | | −10.2 | | | | |
| ILE | −9.6 | −10 | | | | |
| LEU | | −9.8 | −9.6 | | | |
| LYS | | | | | | |
| MET | | | | | | |
| PHE | −10.1 | −10.9 | | | | |
| PRO | | −9.7 | | | | |
| SER | | | | | | |
| THR | | −9.8 | | | | |
| TRP | −9.6 | | −10.1 | | | |
| TYR | −9.6 | −11 | −9.8 | | | |
| VAL | | | | | | |

Block S140 can include determining one or more peptide sequence motifs based on the binding parameters for the reengineered peptide sequences; and/or identifying one or more peptides (e.g., for use in a therapeutic composition) based on the one or more peptide sequence motifs.

For example, Block S140 can include selecting a peptide sequence motif (e.g., based on results shown in Table 2) of [X][Z][B]APW (SEQ ID NOS:6-245), where X can correspond to at least one or more of (I,F,W,Y,A), Z can correspond to at least one or more of (D,A,Q,E,G,H,I,L,F,P,T,Y), B can correspond to at least one or more of (Q,L,W,Y), and where the bolded amino acids can be conserved. However, any suitable peptide sequence motifs can be derived from reengineering the ADQAPW (SEQ ID NO:198) peptide sequence and/or peptide, and/or reengineering any other suitable peptide sequence and/or peptide.

TABLE 3

Mutants of PPPIANP (SEQ ID NO: 693) peptide (in kcal/mol)

| | PRO1 | PRO2 | PRO3 | ILE4 | ALA5 | ASN6 | PRO7 |
|---|---|---|---|---|---|---|---|
| ALA | | | | −10.9 | | | |
| ARG | | | | | | | |
| ASN | | | | | | | |
| ASP | | | | | | −10.5 | |
| CYS | | | | | −10.6 | −10.3 | |
| GLN | | | | | −10.3 | | |
| GLU | | | | | −10.3 | | |
| GLY | | | | | −10.3 | −10.4 | −10.4 |
| HIS | | | | | −10.4 | | |
| ILE | | | | | | −10.9 | |
| LEU | | | | | −10.5 | | |
| LYS | | | | | | | |

TABLE 3-continued

Mutants of PPPIANP (SEQ ID NO: 693) peptide (in kcal/mol)

| | PRO1 | PRO2 | PRO3 | ILE4 | ALA5 | ASN6 | PRO7 |
|---|---|---|---|---|---|---|---|
| MET | | | | | | | |
| PHE | | | | -11 | -10.6 | | |
| PRO | | | | | -10.6 | | |
| SER | | | | -10.5 | | | |
| THR | | | | -10.6 | | | |
| TRP | | | | -11.6 | -11.1 | | |
| TYR | | | -11.2 | -11.3 | | | |
| VAL | | | | -10.8 | | | |

Block S140 can include selecting a peptide sequence motif (e.g., based on results shown in Table 3) of PP[X][Z][B][O]P (SEQ ID NOS:246-693), where X can correspond to at least one or more of (Y,P), Z can correspond to at least one or more of (W,Y,F,A,V,C,T,L,S,H,Q,E,G,I), B can correspond to at least one or more of (W,I,F,P,D,G,C,A), O can correspond to at least one or more of (G,N), and where the bolded amino acids can be conserved. However, any suitable peptide sequence motifs can be derived from reengineering the PPPIANP (SEQ ID NO:693) peptide sequence and/or peptide, and/or reengineering any other suitable peptide sequence and/or peptide.

TABLE 4

Mutants of WLGFQVY (SEQ ID NO: 35253) peptide (in kcal/mol)

| | TRP1 | LEU2 | GLY3 | PHE4 | GLN5 | VAL6 | TYR7 |
|---|---|---|---|---|---|---|---|
| ALA | | | | | -9.8 | -9.9 | |
| ARG | | -9.7 | | | | -10.1 | |
| ASN | | | | | | | |
| ASP | | | | | -10.4 | -9.7 | |
| CYS | | | | | | -10.1 | |
| GLN | | | | | | -9.9 | |
| GLU | | | | | | | |
| GLY | -9.7 | | | | -10.1 | | |
| HIS | | | | -9.8 | | | |
| ILE | | -9.8 | -9.7 | | -10.6 | | |
| LEU | | | | -9.7 | | -10 | |
| LYS | | | | | | | |
| MET | | -9.7 | | | | | |
| PHE | | -9.8 | | | -10.3 | -10.6 | -10.2 |
| PRO | | | | -10 | | | |
| SER | | -9.7 | | | | | |
| THR | | | | | | -10.2 | |
| TRP | | -10.4 | | | | | |
| TYR | -9.7 | | | | -10.1 | -10.4 | |
| VAL | | -10.2 | | | | -10.3 | |

Block S140 can include selecting a peptide sequence motif (e.g., based on results shown in Table 4) of [X][Z][i][O][B][J][f] (SEQ ID NOS:694-35253), where X can correspond to at least one or more of (G,Y,W), Z can correspond to at least one or more of (W,V,I,F,R,M,S,L), i can correspond to at least one or more of (I,G), O can correspond to at least one or more of (Y,P,H,L,F), B can correspond to at least one or more of (I,D,Y,F,V,T,G,A,Q), J can correspond to at least one or more of (F,R,C,L,A,Q,D,V) and f can correspond to at least one or more of (F,Y). However, any suitable peptide sequence motifs can be derived from reengineering the WLGFQVY (SEQ ID NO:35253) peptide sequence and/or peptide, and/or reengineering any other suitable peptide sequence and/or peptide.

In the example, the second target set of peptide sequences and/or peptides (e.g., derived from Rv1168c and targeting the first site, etc.) can additionally or alternatively include (e.g., based on best performing affinity to the first site, etc.)

FSPPAPI (SEQ ID NO:35269) (e.g., -11.0 kcal/mol), DFTIFPP (SEQ ID NO:35271) (e.g., -10.9 kcal/mol) and HTPAIFA (SEQ ID NO:35283) (e.g., -10.0 kcal/mol), where reengineering the second target set can result in binding energies (e.g., derived from molecular docking results, etc.) shown in Tables 5, 6, and 7.

TABLE 5

Mutants of FSPPAPI (SEQ ID NO: 35269) peptide (in kcal/mol)

| | PHE1 | SER2 | PRO3 | PRO4 | ALA5 | PRO6 | ILE7 |
|---|---|---|---|---|---|---|---|
| ALA | | | | | | | -11 |
| ARG | | | | | | | |
| ASN | | | | | | | |
| ASP | | | | | | | |
| CYS | | | | | | | |
| GLN | | | | | | | |
| GLU | | | | | | | -11 |
| GLY | | | | | | | -11 |
| HIS | | | | | | | |
| ILE | | | | | | | |
| LEU | | | | | | | -11.4 |
| LYS | | | | | | | |
| MET | | | | | | | |
| PHE | | | | | | | |
| PRO | | -11.7 | | | | | -11.7 |
| SER | | | | | | | |
| THR | | | | | | | |
| TRP | | | | | | | |
| TYR | | | | | | | -11.6 |
| VAL | | | | | | | -11 |

Block S140 can include selecting a peptide sequence motif (e.g., based on results shown in Table 5) of F[X]PPAP[J] (SEQ ID NOS:35254-35269), where X can correspond to at least one or more of (P,S), J can correspond to at least one of (P,Y,L,A,E,G,V,I), and where the bolded amino acids can be conserved. However, any suitable peptide sequence motifs can be derived from reengineering the FSPPAPI (SEQ ID NO:35269) peptide sequence and/or peptide, and/or reengineering any other suitable peptide sequence and/or peptide.

TABLE 6

Mutants of DFTIFPP (SEQ ID NO: 35271) peptide (in kcal/mol)

| | ASP1 | PHE2 | THR3 | ILE4 | PHE5 | PRO6 | PRO7 |
|---|---|---|---|---|---|---|---|
| ALA | | | | | | | |
| ARG | | | | | | | |
| ASN | | | | | | | |
| ASP | | | | | | | |
| CYS | | | | | | | |
| GLN | | | | | | | |
| GLU | | | | | | | |
| GLY | | | | | | | |
| HIS | | | | | | | |
| ILE | | | | | | | |
| LEU | | | | | | | |
| LYS | | | | | | | |
| MET | | | | | | | |
| PHE | | | | | | | |
| PRO | | | | | | | |
| SER | | | | | | | |
| THR | | | | | | | |
| TRP | | | | | | | |
| TYR | | | | | | | |
| VAL | | | | -11.1 | | | |

Block S140 can include selecting a peptide sequence motif (e.g., based on results shown in Table 6) of DFT[X]FPP (SEQ ID NOS:35270-35271), where X can correspond to at least one or more of (V,I) and where the bolded amino acids can be conserved. However, any suitable peptide sequence motifs can be derived from reengineering the DFTIFPP (SEQ ID NO:35271) peptide sequence and/or peptide, and/or reengineering any other suitable peptide sequence and/or peptide.

TABLE 7

Mutants of HTPAIFA (SEQ ID NO: 35283) peptide (in kcal/mol)

| | HIS1 | THR2 | PRO3 | ALA4 | ILE5 | PHE6 | ALA7 |
|---|---|---|---|---|---|---|---|
| ALA | | | | | | | |
| ARG | | | | | | | |
| ASN | | | | | | | |
| ASP | | | | | | | |
| CYS | | | | | | | |
| GLN | | | | | | | |
| GLU | | | | | | | |
| GLY | | | | | | | |
| HIS | | | | | -10.4 | | |
| ILE | | | | | | | |
| LEU | | | | | | | |
| LYS | | | | | | | |
| MET | | | | | | | |
| PHE | | | | | | | |
| PRO | | | | | | | |
| SER | | | | | | | |
| THR | -10 | | | | | | |
| TRP | | | | | | | |
| TYR | -10.2 | | | | | | -10.4 |
| VAL | | | | | | | |

Block S140 can include selecting a peptide sequence motif (e.g., based on results shown in Table 7) of [X]TPA[J]F[B] (SEQ ID NOS:35272-35283), where X can correspond to at least one or more of (Y,T,H), J can correspond to at least one or more of (H,I), B can correspond to at least one or more of (Y,A), and where the bolded amino acids can be conserved. However, any suitable peptide sequence motifs can be derived from reengineering the HTPAIFA (SEQ ID NO:35283) peptide sequence and/or peptide, and/or reengineering any other suitable peptide sequence and/or peptide.

In the example, the third target set of peptide sequences and/or peptides (e.g., derived from Rv1168c and targeting the second site, etc.) can additionally or alternatively include (e.g., based on best performing affinity to the second site, etc.) AARLTPFSPP (SEQ ID NO:35303) (−7.5 kcal/mol), where reengineering the third target set can result in binding energies (e.g., derived from molecular docking results, etc.) shown in Table 8.

TABLE 8

Mutants of AARLTPFSPP (SEQ ID NO: 35303) peptide (in kcal/mol)

| | ALA1 | ALA2 | ARG3 | LEU4 | THR5 | PRO6 | PHE7 | SER8 | PRO9 | PRO10 |
|---|---|---|---|---|---|---|---|---|---|---|
| ALA | | | | -7.8 | | | | | | |
| ARG | | | | | | | | | | |
| ASN | | | | -7.5 | | | | | | |
| ASP | | | | | | | | | | |
| CYS | | | | | | | | | | |
| GLN | | | | | | | | | | |
| GLU | | | | | | | | | | |
| GLY | | | | | | | | | | |
| HIS | | | | | | | | | | |
| ILE | | | | | | | | | | |
| LEU | | | | | | | | | | |
| LYS | | | | | | | | | | |
| MET | | | | | | | | | | |
| PHE | | | | | | | | | | |
| PRO | -7.5 | | | -7.6 | | | | -7.7 | | |
| SER | | | | | | | | | | |
| THR | | | | | | | | | | |
| TRP | | | | -7.6 | | | | | | |
| TYR | | | | | | | | | | |
| VAL | | | | | | | | | | |

Block S140 can include selecting a peptide sequence motif (e.g., based on results shown in Table 8) of [B]AR [X]TP[Z]SPP (SEQ ID NOS:35284-35303), where B can correspond to at least one or more of (P,A), X can correspond to at least one or more of (A,P,W,N,L), Z can correspond to at least one or more of (P,F), and where the bolded amino acids can be conserved. However, any suitable peptide sequence motifs can be derived from reengineering the AARLTPFSPP (SEQ ID NO:35303) peptide sequence and/or peptide, and/or reengineering any other suitable peptide sequence and/or peptide.

In the example, the fourth target set of peptide sequences and/or peptides (e.g., derived from Amuc_1100 and targeting the second site, etc.) can additionally or alternatively include (e.g., based on best performing affinity to the second site, etc.) LETAYKPF (SEQ ID NO:37718) (−7 kcal/mol), AAPAAPAIQQ (SEQ ID NO:35803) (−7.1 kcal/mol), and HFNQPKAQEP (SEQ ID NO:35839) (−7 kcal/mol), where reengineering the fourth target set can result in binding energies (e.g., derived from molecular docking results, etc.) shown in Tables 9, 10, and 11.

TABLE 9

| Mutants of LETAYKPF (SEQ ID NO: 37718) peptide (in kcal/mol) | | | | | | | |
|---|---|---|---|---|---|---|---|
| | LEU1 | GLU2 | THR3 | ALA4 | TYR5 | LYS6 | PRO7 | PHE8 |
| ALA | | −7.4 | | | | | | |
| ARG | | | | | | | | |
| ASN | | −7.2 | | | | | | |
| ASP | | | | | | | | |
| CYS | | | | | | | | |
| GLN | | | | | | | | |
| GLU | | | | | | | | |
| GLY | | | | | | | | |
| HIS | | | | | | | | |
| ILE | | | | | | | | |
| LEU | | | | | | | | |
| LYS | | | | | | | | |
| MET | | | | | | | | |
| PHE | | | | | | | | |
| PRO | | | | | | | | |
| SER | | −7.1 | | | | | | −7 |
| THR | | | | | | | | |
| TRP | −7.3 | −7.1 | | | | | | |
| TYR | | | | | | | | |
| VAL | | | | | | | | |

Block S140 can include selecting a peptide sequence motif (e.g., based on results shown in Table 9) of [X][J]TAYKP[B] (SEQ ID NOS:35304-35323), where X can correspond to at least one or more of (W,L), J can correspond to at least one or more of (A,N,S,W,E), B can correspond to at least one or more of (S,F), and where the bolded amino acids can be conserved. However, any suitable peptide sequence motifs can be derived from reengineering the LETAYKPF (SEQ ID NO:37718) peptide sequence and/or peptide, and/or reengineering any other suitable peptide sequence and/or peptide.

TABLE 10

| Mutants of AAPAAPAIQQ (SEQ ID NO: 35803) peptide (in kcal/mol) | | | | | | | | | |
|---|---|---|---|---|---|---|---|---|---|
| | ALA1 | ALA2 | PRO3 | ALA4 | ALA5 | PRO6 | ALA7 | ILE8 | GLN9 | GLN10 |
| ALA | | | | | | | | | | |
| ARG | | | | | | | | | | −7.2 |
| ASN | | | | −7.1 | | | | | | |
| ASP | | | | | | | | | | |
| CYS | | | | | | | | | | |
| GLN | −7.1 | | | | | | | | | |
| GLU | | | | | | | | | | |

TABLE 10-continued

Mutants of AAPAAPAIQQ (SEQ ID NO: 35803) peptide (in kcal/mol)

| | ALA1 | ALA2 | PRO3 | ALA4 | ALA5 | PRO6 | ALA7 | ILE8 | GLN9 | GLN10 |
|---|---|---|---|---|---|---|---|---|---|---|
| GLY | | | | | | | | | | |
| HIS | | | | -7.2 | | | | | | |
| ILE | | | | | | | | | | |
| LEU | | | | | | | | | | |
| LYS | | | | | | | | | | |
| MET | | | | | | | | | | |
| PHE | | | -7.2 | | | | | | | |
| PRO | | | | | -7.3 | | | | | |
| SER | | | | | | | | | | |
| THR | | | | | | | | | | |
| TRP | -7.1 | | | | -7.1 | | | | -7.2 | |
| TYR | | | -7.1 | -7.2 | | -7.5 | | | | |
| VAL | | | | | | | | | | |

Block S140 can include selecting a peptide sequence motif (e.g., based on results shown in Table 10) of [X]A[J][B]AP[Z]I[O][U] (SEQ ID NOS:35324-35803), where X can correspond to at least one or more of (N,W,A), J can correspond to at least one or more of (F,N,Y,P), B can correspond to at least one or more of (P,H,Y,W,A), Z can correspond to at least one or more of (Y,A), O can correspond to at least one or more of (W,Q), U can correspond to at least one or more of (R, Q), and where the bolded amino acids can be conserved. However, any suitable peptide sequence motifs can be derived from reengineering the LETAYKPF (SEQ ID NO:37718) peptide sequence and/or peptide, and/or reengineering any other suitable peptide sequence and/or peptide.

The peptide sequence motifs described herein, peptide sequences, and/or peptides are preferably of any suitable length, such as where any number and/or type of amino acids can be included at the ends of the peptide sequence motifs, peptide sequences, and/or peptides. For example, Block S140 can include determining peptide sequence motifs based on Amuc_1100 (e.g., native peptide sequences of peptides of Amuc_1100, etc.), where the peptide sequence motifs can include one or more of: n[X][Z][B]APWn (SEQ ID NOS:6-245), nPP[X][Z][B][O]Pn (SEQ ID NOS:246-693), n[X][Z][i][O][B][J][f]n (SEQ ID NOS:694-35253), n[X][J]TAYKP[B]n (SEQ ID NOS:35304-35323), n[X]A[J][B]AP[Z]I[O][U]n (SEQ ID NOS:35324-35803), and nH[X][J]QP[B]AQEPn (SEQ ID NOS:35804-35839), and

TABLE 11

Mutants of HFNQPKAQEP (SEQ ID NO: 35839) peptide (in kcal/mol)

| | HIS1 | PHE2 | ASN3 | GLN4 | PRO5 | LYS6 | ALA7 | GLN8 | GLU9 | PRO10 |
|---|---|---|---|---|---|---|---|---|---|---|
| ALA | | -7.3 | | | | | | | | |
| ARG | | | | | | | | | | |
| ASN | | | | | | | | | | |
| ASP | | | | | | | | | | |
| CYS | | | | | | | | | | |
| GLN | | | | | | | | | | |
| GLU | | -7.1 | | | | | | | | |
| GLY | | -7.1 | -7.5 | | | | | | | |
| HIS | | | | | -7.6 | | | | | |
| ILE | | | | | | | | | | |
| LEU | | | | | | | | | | |
| LYS | | | | | | | | | | |
| MET | | | | | | | | | | |
| PHE | | | | | | | | | | |
| PRO | | | | | | | | | | |
| SER | | | | | | | | | | |
| THR | | | | | | | | | | |
| TRP | | -7 | | | -7 | | | | | |
| TYR | | | | | | | | | | |
| VAL | | | | | | | | | | |

Block S140 can include selecting a peptide sequence motif (e.g., based on results shown in Table 11) of H[X][J]QP[B]AQEP (SEQ ID NOS:35804-35839), where X can correspond to at least one or more of (E,G,W,F), J can correspond to at least one or more of (G,A,N), B can correspond to at least one or more of (H,W,K), and where the bolded amino acids can be conserved. However, any suitable peptide sequence motifs can be derived from reengineering the HFNQPKAQEP (SEQ ID NO:35839) peptide sequence and/or peptide, and/or reengineering any other suitable peptide sequence and/or peptide.

where "n" can correspond to any number and type of amino acids (e.g., including n=0). In another example, Block S140 can include determining peptide sequence motifs based on Rv1168c (e.g., native peptide sequences of peptides of Rv1168c, etc.), where the peptide sequence motifs can include one or more of: n[B]AR[X]TP[Z]SPPn (SEQ ID NOS:35284-35303), nF[X]PPAP[J]n (SEQ ID NOS:35254-35269), nDFT[X]FPPn (SEQ ID NOS:35270-35271), and n[X]TPA[J]F[B]n (SEQ ID NOS:35272-35283), and where "n" can correspond to any number and type of amino acids (e.g., including n=0). Additionally or alternatively, any number and/or type of amino acids can be added (e.g., at one or more ends of a peptide sequence, at a position within the peptide sequence, etc.), deleted (e.g., any subset combination of amino acids of peptide sequences, etc.), and or otherwise modified (e.g., mutated to any other suitable amino acid), at any position of the peptide sequences.

In an example, Block S140 can include determining a therapeutic composition binding to TLR2 in the LRR 15-19 section and in the LRR 11-13 section (e.g., the first site and the second site, etc.).

In a variation, Block S140 can include determining a patient microbiome analysis (e.g., associated with the TLR-related condition; etc.) based on a sample from the patient (e.g., based on sequencing the sample and/or analyzing at least one of microbiome composition features, microbiome functional features, microbiome pharmacogenomics features, and/or other suitable features for the patient; etc.), where identifying a peptide for a therapeutic composition can be based on the patient microbiome analysis, binding parameters for reengineered peptide sequences, and/or any other suitable parameters.

However, determining peptide sequence motifs, target peptide sequences and/or peptides, and/or any other suitable components associated with therapeutic compositions can be performed in any suitable manner.

The compositions (e.g., including peptides, biomolecules, associated peptide sequences, associated peptide sequence motifs, etc.), methods 100, and systems 200 described herein can be determined, generated, and applied without undue experimentation. Further, any biomolecules with chemical and/or physiological relatedness to aspects described herein can be substituted and/or otherwise used.

The method 100 and/or system 200 of the embodiments can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a patient computer or mobile device, or any suitable combination thereof. Other systems 200 and methods 100 of the embodiments can be embodied and/or implemented at least in part as a machine configured to receive a computer-readable medium storing computer-readable instructions. The instructions can be executed by computer-executable components integrated by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor, though any suitable dedicated hardware device can (alternatively or additionally) execute the instructions.

The FIGURES illustrate the architecture, functionality and operation of possible implementations of compositions, methods 100, and systems 200 according to preferred embodiments, example configurations, and variations thereof. It should also be noted that, in some alternative implementations, the functions noted can occur out of the order noted in the FIGURES. For example, aspects shown in succession may, in fact, be executed substantially concurrently, or the aspects may sometimes be executed in the reverse order, depending upon the functionality involved. The embodiments include every combination and permutation of the various system components and the various method processes, including any variations, examples, and specific examples. As a person skilled in the art will recognize from the previous detailed description and from the figures and claims, modifications and changes can be made to the embodiments without departing from the scope.

TABLE 12

Amino Acids

| 1-Letter Symbol | 3-Letter Symbol | Meaning |
|---|---|---|
| A | Ala | Alanine |
| C | Cys | Cysteine |
| D | Asp | Aspartic Acid |
| E | Glu | Glutamic Acid |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophan |
| Y | Tyr | Tyrosine |
| X | Xaa | unknown or other or none |

4. Additional or Alternative Examples

In variations, the method 100 and/or system 200 can apply one or more experiments to assess the activation of TLR2 receptors mediated by protein fragments and/or peptides. Any of the variants described herein (e.g., embodiments, variations, examples, specific examples, illustrations, etc.) and/or any portion of the variants described herein can be additionally or alternatively combined, excluded, and/or otherwise applied.

In a specific example, stimulation of TLR2 receptors mediated by protein fragments and/or peptides were assessed using HEK-Blue cells that overexpress TLR2. For the immune receptor stimulation analysis HEK-Blue hTLR2 and HEK-Blue™ Null1 (parental cell line) cell lines were used. Stimulation of the receptors with the corresponding ligands activates NF-κB and AP-1, which induces the production of secreted embryonic alkaline phosphatase (SEAP), the levels of which were measured by spectrophotometer. All cell lines were grown and subcultured up to 70-80% of confluency using as a maintenance medium Dulbecco's Modified Eagle Medium (DMEM) supplemented with 4.5 g/l D-glucose, 50 U/ml penicillin, 50 µg/ml streptomycin, 100 µg/ml Normocin, 2 mM L-glutamine and 10% (v/v) of heat-inactivated FBS. For each cell line, an immune response experiment was carried out by seeding HEK-blue cells in flat-bottom 96-well plates and stimulating them by addition of the peptides (see table 1). The 96-well plates were incubated for 16-18 h at 37° C. in a 5% CO2 incubator. Zymosan (10 ug/ml for hTLR2), was used as positive control whereas maintenance medium (DMEM) without any selective antibiotics was used as negative control. SEAP secretion was detected by measuring the OD630 at 1 h after addition of 180 µL of QUANTI-Blue (Invivogen) to 20 µL of induced HEK-Blue hTLR2/Null supernatant. Protein fragments from Amuc to be assessed in HEK-Blue cells were obtained by an expression plasmid for the production of His-tagged Amuc_1100 (full protein and its fragments), was constructed by amplification of its gene devoid of the coding sequence for its signal sequence and cloning of the resulting PCR product in pET-28a *E. coli* XL1Blue. The following primer sequences were used to obtain protein full, first fragment and second fragment of Amuc_1100:

TABLE 13

Primer sequences used to obtain protein full, first fragment and second fragment of Amuc_1100

| Name | Primer sequence |
| --- | --- |
| Complete amuC_1100 | GGGTACCATATGATCGTCAATTCCAAACGC (SEQ ID NO: 37712) <br> CCTTGGCTCGAGTTAATCTTCAGACGGTTCCTG (SEQ ID NO: 37713) |
| Fragment 1 amuC_1100 | GGGTACCATATGATCGTCAATTCCAAACGC (SEQ ID NO: 37714) <br> CCTTGGCTCGAGAATGGGGAGCTGGGGCG (SEQ ID NO: 37715) |
| Fragment 2 amuC_1100 | GGGTACCATATGCTGGCGGAATGCGGCCTG (SEQ ID NO: 37716) <br> CCTTGGCTCGAGTTAATCTTCAGACGGTTCCTG (SEQ ID NO: 37717) |

Bolded sequences are restriction sites for NdeI and XhoI enzymes.

Conformation of the resulting plasmid pET-28a-1100 was verified by polymerase chain reaction (PCR), sequencing analysis and transformed into *E. coli* BL21 (DE3). This strain was then grown in LB-broth containing kanamycin (50 μg/ml) with shaking at 220 rpm at 37° C., followed by induction through the addition of 1 mM IPTG in the growth medium during mid-exponential phase. After three hours of induction, cells were pelleted by centrifuging 10 min at 5,000 g and cell pellets stored at −20° C. until lysis. Cell pellets were resuspended and lysed using lysozyme and frozen −80° C. and heat 37° C. Supernatant was collected after centrifugation and the Amuc_1100 was purified by nickel column affinity. The protein visualization and quantification was determined by SDS-Page and bradford method, respectively. The Amuc_1100 protein was stored at −20° C.

Figure 4:
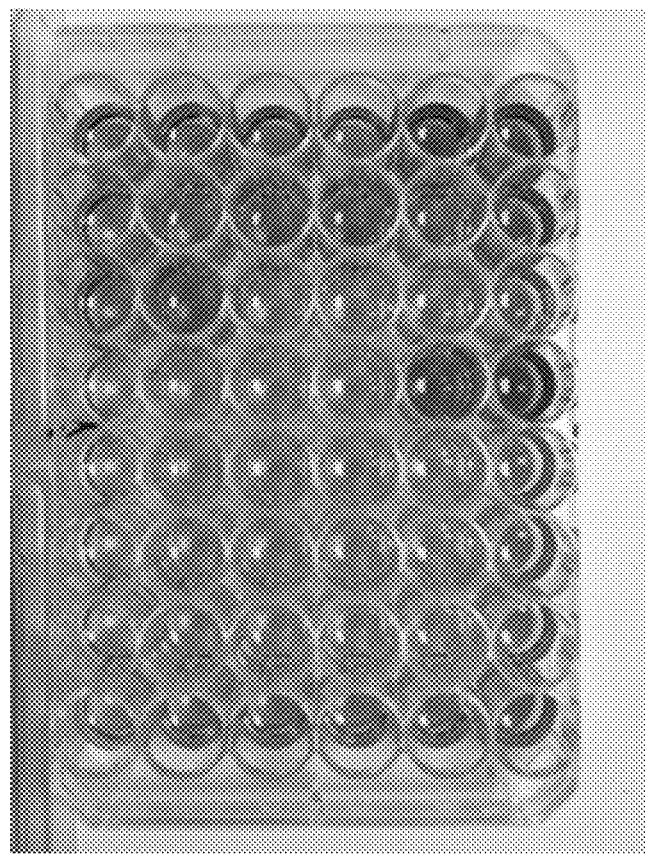
FIG. 4 illustrates a specific example of experimental results with a 96-well plate seeded with HEK-TLR2 cells, and where different fragments of Amuc_1100 protein were assayed.

In Table 14 and FIG. 4, results are informed as positive TLR2 activation (e.g., purple color or darker color) or no TLR2 activation (e.g. pink color or lighter color). Three fragments of Amuc_1100 were tested: Fragment 1, Fragment 2 and Fragment 3, where the first one contains the fragments 2 and 3. Fragments 2 and 3 share a region nXXGFXLKAINSLVN[KR]LA[ED]CGLSKFIKVY[KR]PQLPIETPA[ND][NE]XXXn (SEQ ID NO:37737), where the notation "X" can indicate any amino acid (e.g., a defined set of amino acids, non-natural amino acid, etc.) and/or no amino acid (e.g., where X is deleted, where one or more mother molecules are inserted, included, and/or otherwise added, etc.), and n can represent that the fragment (e.g., XXX fragment) can have any length with any suitable added amino acids at any suitable end, which can improve the activation of TLR2 (e.g., as determined by computational calculations and described above, etc.).

TABLE 14

| Experimental Results | |
| --- | --- |
| Section | Results based on the color |
| Fragment 1 (FL) (20 uL) | Positive |
| Fragment 1 (FL) (50 uL) | Positive |
| Control BLB21 | Negative |
| Neg. control | Negative |
| Zymosan (Positive control) | Positive |
| Fragment 2 AmuC | Positive |
| Fragment 3 AmuC | Positive |

FIG. 4 illustrates a 96-well plate seeded with HEK-TLR2 cells. Different fragments of Amuc_1100 protein were assayed. In FIG. 4, the first horizontal line of the plate illustrates from left to right (by duplicate): Fragment 1 AmuC (first extract×2),Fragment 1 AmuC (second extract low concentration×2), Fragment 1 AmuC (second extract high concentration×2). The second line illustrates from left to right (by duplicate): Fragment 2 AmuC (low concentration×2), Fragment 2 AmuC (high concentration×2), Fragment 3 AmuC (low concentration×2). The third line illustrates from left to right (by duplicate): Section 2 AmuC (high concentration×2), Control BLB21 (*E. coli*×2), Control II. The fourth line illustrates from left to right (by duplicate): Control imidazole (protein purification×2), Negative control (medium×2),Positive control (Zymosan×2). The fifth through eighth lines illustrate the same, but with parental cell line (HEK 293 Null), used as control.

SEQUENCE LISTING

The patent contains a lengthy sequence listing. A copy of the sequence listing is available in electronic form from the USPTO web site (https://seqdata.uspto.gov/?pageRequest=docDetail&DocID=US11931400B2). An electronic copy of the sequence listing will also be available from the USPTO upon request and payment of the fee set forth in 37 CFR 1.19(b)(3).

We claim:

1. A therapeutic composition for improving a Toll-like receptor (TLR)-related condition, the therapeutic composition comprising a peptide configured to modulate TLR-related functionality and derived based on reengineering of a target peptide sequence associated with a microorganism-related modulator associated with Amuc_1100 protein from *Akkermansia muciniphila*, wherein the peptide corresponds to a peptide sequence comprising at least one motif of a set of peptide sequence motifs comprising:

a first motif comprising XXGFXLKXX (SEQ ID NO: 1), wherein X in the first motif comprises any amino acid type or no amino acid;

a second motif comprising XXTPA[Z][B]XXX (SEQ ID NOS:2-5), wherein X in the second motif comprises any amino acid type or no amino acid, wherein Z in the second motif comprises at least one of (N,D), and wherein B in the second motif comprises at least one of (N,E);

a third motif comprising [X][Z][B]APW (SEQ ID NOS: 6-245), wherein X in the third motif comprises at least one of (I,F,W,Y,A), wherein Z in the third motif comprises at least one of (D,A,Q,E,G,H,I,L,F,P,T,Y), and wherein B in the third motif comprises at least one of (Q,L,W,Y);

a fourth motif comprising PP[X][Z][B][O]P (SEQ ID NOS:246-693), wherein X in the fourth motif comprises at least one of (Y,P), wherein Z in the fourth motif comprises at least one of (W,Y,F,A,V,C,T,L,S,H,Q,E,G,I), wherein B in the fourth motif comprises at least one of (W,I,F,P,D,G,C,A), and wherein O in the fourth motif comprises at least one of (G,N);

a fifth motif comprising [X][Z][i][O][B][J][f] (SEQ ID NOS: 694-35253), wherein X in the fifth motif comprises at least one of (G,Y,W), wherein Z in the fifth motif comprises at least one of (W,V,I,F,R,M,S,L), wherein i in the fifth motif comprises at least one of (I,G), wherein O in the fifth motif comprises at least one of (Y,P,H,L,F), wherein B in the fifth motif comprises at least one of (I,D,Y,F,V,T,G,A,Q), wherein J in the fifth motif comprises at least one of (F,R,C,L,A,Q,D,V), and wherein f in the fifth motif comprises at least one of (F,Y);

a tenth motif comprising [X][J]TAYKP[B] (SEQ ID NOS: 35304-35323), wherein X in the tenth motif comprises at least one of (W,L), wherein J in the tenth motif comprises at least one of (A,N,S,W,E), and wherein B in the tenth motif comprises at least one of (S,F);

an eleventh motif comprising [X]A[J][B]AP[Z]I[O][U] (SEQ ID NOS:35324-35803), wherein X in the eleventh motif comprises at least one of (N,W,A), wherein J in the eleventh motif comprises at least one of (F,N,Y,P), wherein B in the eleventh motif comprises at least one of (P,H,Y,W,A), wherein Z in the eleventh motif comprises at least one of (Y,A), wherein O in the eleventh motif comprises at least one of (W,Q), and wherein U in the eleventh motif comprises at least one of (R, Q); and a twelfth motif comprising H[X][J]QP[B]AQEP (SEQ ID NOS:35804-35839), wherein X in the twelfth motif comprises at least one of (E,G,W,F), wherein J in the twelfth motif comprises at least one of (G,A,N), and wherein B in the twelfth motif comprises at least one of (H,W,K).

2. The therapeutic composition of claim 1, wherein the peptide is derived based on reengineering of the target peptide sequence associated with the microorganism-related modulator associated with Amuc_1100 and on a binding parameter value for the peptide for a TLR binding site for Staphylococcal Superantigen-Like protein 3 (SSL3), and wherein the peptide corresponds to the peptide sequence comprising the at least one motif comprising at least one of the third motif, the fourth motif, and the fifth motif.

3. The therapeutic composition of claim 1, wherein the peptide is derived based on reengineering of the target peptide sequence associated with the microorganism-related modulator associated with Amuc_1100 and on a binding parameter value for the peptide for a TLR binding site for a proline-proline glutamic acid protein, and wherein the peptide corresponds to the peptide sequence comprising the at least one motif comprising at least one of the tenth motif, the eleventh motif, and the twelfth motif.

4. A therapeutic composition for improving a Toll-like receptor (TLR)-related condition, the therapeutic composition comprising a peptide configured to modulate TLR-related functionality and derived based on reengineering of a target peptide sequence associated with a microorganism-related modulator associated with Rv1168c protein from *Mycobacterium tuberculosis*, wherein the peptide corresponds to a peptide sequence comprising at least one motif of a set of peptide sequence motifs comprising:

a sixth motif comprising F[X]PPAP[J] (SEQ ID NOS: 35254-35269), wherein X in the sixth motif comprises at least one of (P,S), and wherein J in the sixth motif comprises at least one of (P,Y,L,A,E,G,V,I);

a seventh motif comprising DFT[X]FPP (SEQ ID NOS: 35270-35271), wherein X in the seventh motif comprises at least one of (V,I);

an eighth motif comprising [X]TPA[J]F[B] (SEQ ID NOS:35272-35283), wherein X in the eight motif comprises at least one of (Y,T,H), wherein J in the eight motif comprises at least one of (H,I), and wherein B in the eight motif comprises at least one of (Y,A); and a ninth motif comprising [B]AR[X]TP[Z]SPP (SEQ ID NOS:35284-35303), wherein B in the ninth motif comprises at least one of (P,A), wherein X in the ninth motif comprises at least one of (A,P,W,N,L), and wherein Z in the ninth motif comprises at least one of (P,F).

5. The therapeutic composition of claim 4, wherein the peptide is derived based on reengineering of the target peptide sequence associated with the microorganism-related modulator associated with Rv1168c and on a binding parameter value for the peptide for a TLR binding site for Staphylococcal Superantigen-Like protein 3 (SSL3), and wherein the peptide corresponds to the peptide sequence comprising the at least one motif comprising at least one of the sixth motif, the seventh motif, and the eighth motif.

6. The therapeutic composition of claim 4, wherein the peptide is derived based on reengineering of the target peptide sequence associated with the microorganism-related modulator associated with Rv1168c and on a binding parameter value for the peptide for a TLR binding site for a proline-proline glutamic acid protein, and wherein the peptide corresponds to the peptide sequence comprising the at least one motif comprising the ninth motif.

7. The therapeutic composition of claim 1 or 4, wherein the peptide is configured to modulate TLR2-related functionality and derived based on reengineering of the target peptide sequence associated with a microorganism-related modulator of TLR2, and wherein the TLR-related condition comprises at least one of a metabolic disease and an immune disorder.

8. The therapeutic composition of claim 1 or 4, wherein the peptide corresponds to the peptide sequence with at least 90% identity to a determined peptide sequence comprising the at least one motif of the set of peptide sequence motifs.

9. A therapeutic composition for improving a Toll-like receptor (TLR)-related condition, the therapeutic composition comprising a peptide configured to modulate TLR-related functionality and derived based on reengineering of a target peptide sequence associated with a microorganism-related modulator associated of a TLR, wherein the peptide corresponds to a peptide sequence comprising nXX[MOTIF1][α][α]NS[α][α]N[β]LA[γ]C[AG]LS[β][δ]I[β]V[δ][β][δ]QL[δ]I[γ][MOTIF2]XXn (SEQ ID NOS:35840-35983), wherein α comprises an aromatic type amino acid selected from at least one of F, W and T, wherein β comprises a positive type amino acid selected from at least one of R, H and K, wherein γ comprises a negative type amino acid selected from at least one of D and E, wherein δ comprises any amino acid, except for α, β and γ types, wherein X comprises any amino acid type or no amino acid, wherein n comprises any number and type of amino acid, wherein MOTIF1 comprises a first target motif from a set of peptide sequence motifs, wherein MOTIF2 comprises a second target motif from a set of peptide sequence motifs, and wherein the set of peptide sequence motifs comprising:

a first motif comprising XXGFXLKXX (SEQ ID NO: 1), wherein X in the first motif comprises any amino acid type or no amino acid;

a second motif comprising XXTPA[Z][B]XXX (SEQ ID NOS:2-5), wherein X in the second motif comprises any amino acid type or no amino acid, wherein Z in the second motif comprises at least one of (N,D), and wherein B in the second motif comprises at least one of (N,E);

a third motif comprising [X][Z][B]APW (SEQ ID NOS: 6-245), wherein X in the third motif comprises at least one of (I,F,W,Y,A), wherein Z in the third motif comprises at least one of (D,A,Q,E,G,H,I,L,F,P,T,Y), and wherein B in the third motif comprises at least one of (Q,L,W,Y);

a fourth motif comprising PP[X][Z][B][O]P (SEQ ID NOS:246-693), wherein X in the fourth motif comprises at least one of (Y,P), wherein Z in the fourth motif comprises at least one of (W,Y,F,A,V,C,T,L,S,H,Q,E,G,I), wherein B in the fourth motif comprises at least one of (W,I,F,P,D,G,C,A), and wherein O in the fourth motif comprises at least one of (G,N);

a fifth motif comprising [X][Z][i][O][B][J][f] (SEQ ID NOS: 694-35253), wherein X in the fifth motif comprises at least one of (G,Y,W), wherein Z in the fifth motif comprises at least one of (W,V,I,F,R,M,S,L), wherein i in the fifth motif comprises at least one of (I,G), wherein O in the fifth motif comprises at least one of (Y,P,H,L,F), wherein B in the fifth motif comprises at least one of (I,D,Y,F,V,T,G,A,Q), wherein J in the fifth motif comprises at least one of (F,R,C,L,A,Q,D,V), and wherein f in the fifth motif comprises at least one of (F,Y);

a sixth motif comprising F[X]PPAP[J] (SEQ ID NOS: 35254-35269), wherein X in the sixth motif comprises at least one of (P,S), and wherein J in the sixth motif comprises at least one of (P,Y,L,A,E,G,V,I);

a seventh motif comprising DFT[X]FPP (SEQ ID NOS: 35270-35271), wherein X in the seventh motif comprises at least one of (V,I);

an eighth motif comprising [X]TPA[J]F[B] (SEQ ID NOS:35272-35283), wherein X in the eight motif comprises at least one of (Y,T,H), wherein J in the eight motif comprises at least one of (H,I), and wherein B in the eight motif comprises at least one of (Y,A);

a ninth motif comprising [B]AR[X]TP[Z]SPP (SEQ ID NOS:35284-35303), wherein B in the ninth motif comprises at least one of (P,A), wherein X in the ninth motif comprises at least one of (A,P,W,N,L), and wherein Z in the ninth motif comprises at least one of (P,F);

a tenth motif comprising [X][J]TAYKP[B] (SEQ ID NOS: 35304-35323), wherein X in the tenth motif comprises at least one of (W,L), wherein J in the tenth motif comprises at least one of (A,N,S,W,E), and wherein B in the tenth motif comprises at least one of (S,F);

an eleventh motif comprising [X]A[J][B]AP[Z]I[O][U] (SEQ ID NOS:35324-35803), wherein X in the eleventh motif comprises at least one of (N,W,A), wherein J in the eleventh motif comprises at least one of (F,N,Y,P), wherein B in the eleventh motif comprises at least one of (P,H,Y,W,A), wherein Z in the eleventh motif comprises at least one of (Y,A), wherein O in the eleventh motif comprises at least one of (W,Q), and wherein U in the eleventh motif comprises at least one of (R, Q); and a twelfth motif comprising H[X][J]QP[B]AQEP (SEQ ID NOS:35804-35839), wherein X in the twelfth motif comprises at least one of (E,G,W,F), wherein J in the twelfth motif comprises at least one of (G,A,N), and wherein B in the twelfth motif comprises at least one of (H,W,K).

10. A therapeutic composition for improving a Toll-like receptor (TLR)-related condition, the therapeutic composition comprising a peptide configured to modulate TLR-related functionality and derived based on reengineering of a target peptide sequence associated with a microorganism-related modulator associated of a TLR, wherein the peptide corresponds to a peptide sequence comprising a combination of at least three motifs from a set of peptide sequence motifs, wherein the peptide corresponds to the peptide sequence comprising nXX[MOTIF1]nX[MOTIF2]nX[MOTIF3]XXn (SEQ ID NOS:35984-37711), wherein X comprises any amino acid type or no amino acid, wherein n comprises any number and type of amino acid, and wherein the set of peptide sequence motifs comprising:

a first motif comprising XXGFXLKXX (SEQ ID NO: 1), wherein X in the first motif comprises any amino acid type or no amino acid;

a second motif comprising XXTPA[Z][B]XXX (SEQ ID NOS:2-5), wherein X in the second motif comprises any amino acid type or no amino acid, wherein Z in the second motif comprises at least one of (N,D), and wherein B in the second motif comprises at least one of (N,E);

a third motif comprising [X][Z][B]APW (SEQ ID NOS: 6-245), wherein X in the third motif comprises at least one of (I,F,W,Y,A), wherein Z in the third motif comprises at least one of (D,A,Q,E,G,H,I,L,F,P,T,Y), and wherein B in the third motif comprises at least one of (Q,L,W,Y);

a fourth motif comprising PP[X][Z][B][O]P (SEQ ID NOS:246-693), wherein X in the fourth motif comprises at least one of (Y,P), wherein Z in the fourth motif comprises at least one of (W,Y,F,A,V,C,T,L,S,H,Q,E,G,I), wherein B in the fourth motif comprises at least one of (W,I,F,P,D,G,C,A), and wherein O in the fourth motif comprises at least one of (G,N);

a fifth motif comprising [X][Z][i][O][B][J][f] (SEQ ID NOS: 694-35253), wherein X in the fifth motif comprises at least one of (G,Y,W), wherein Z in the fifth motif comprises at least one of (W,V,I,F,R,M,S,L), wherein i in the fifth motif comprises at least one of (I,G), wherein O in the fifth motif comprises at least one of (Y,P,H,L,F), wherein B in the fifth motif comprises at least one of (I,D,Y,F,V,T,G,A,Q), wherein J in the fifth motif comprises at least one of (F,R,C,L,A,Q,D,V), and wherein f in the fifth motif comprises at least one of (F,Y);

a sixth motif comprising F[X]PPAP[J] (SEQ ID NOS: 35254-35269), wherein X in the sixth motif comprises at least one of (P,S), and wherein J in the sixth motif comprises at least one of (P,Y,L,A,E,G,V,I);

a seventh motif comprising DFT[X]FPP (SEQ ID NOS: 35270-35271), wherein X in the seventh motif comprises at least one of (V,I);

an eighth motif comprising [X]TPA[J]F[B] (SEQ ID NOS:35272-35283), wherein X in the eight motif comprises at least one of (Y,T,H), wherein J in the eight motif comprises at least one of (H,I), and wherein B in the eight motif comprises at least one of (Y,A);

a ninth motif comprising [B]AR[X]TP[Z]SPP (SEQ ID NOS:35284-35303), wherein B in the ninth motif comprises at least one of (P,A), wherein X in the ninth motif comprises at least one of (A,P,W,N,L), and wherein Z in the ninth motif comprises at least one of (P,F);

a tenth motif comprising [X][J]TAYKP[B] (SEQ ID NOS: 35304-35323), wherein X in the tenth motif comprises at least one of (W,L), wherein J in the tenth motif comprises at least one of (A,N,S,W,E), and wherein B in the tenth motif comprises at least one of (S,F);

an eleventh motif comprising [X]A[J][B]AP[Z]I[O][U] (SEQ ID NOS:35324-35803), wherein X in the eleventh motif comprises at least one of (N,W,A), wherein J in the eleventh motif comprises at least one of (F,N,Y,P), wherein B in the eleventh motif comprises at least one of (P,H,Y,W,A), wherein Z in the eleventh motif comprises at least one of (Y,A), wherein O in the eleventh motif comprises at least one of (W,Q), and wherein U in the eleventh motif comprises at least one of (R, Q); and a twelfth motif comprising H[X][J]QP[B]AQEP (SEQ ID NOS:35804-35839), wherein X in the twelfth motif comprises at least one of (E,G,W,F), wherein J in the twelfth motif comprises at least one of (G,A,N), and wherein B in the twelfth motif comprises at least one of (H,W,K).

11. The therapeutic composition of claim 1 or 4, further comprising a carrier configured to at least one of encapsulate and covalently-conjugate with the peptide, wherein the carrier comprises at least one: a micelle, a polymer, a liposome, a dendrimer, a metallic nanoparticle, a microsphere, a polyelectrolyte complex, an emulsion, a hydrogel, and an injectable polymer.

12. The therapeutic composition of claim 11, wherein the peptide is modified, to improve stability and prevent degradation, with at least one of: an unnatural amino acid, acetylation, and PEGylation.

\* \* \* \* \*